United States Patent
Hasumi et al.

[11] Patent Number: 6,087,924
[45] Date of Patent: Jul. 11, 2000

[54] GAS SENSORS AND METHODS OF MANUFACTURING THE SAME

[75] Inventors: Kazuhisa Hasumi, Odawara; Kentaro Nagano, Yokohama; Hideyuki Horiuchi, Odawara; Osamu Okada, Osakasayama, all of Japan

[73] Assignees: Mikuni Corporation, Tokyo; Osaka Gas Co., Ltd., Osaka, both of Japan

[21] Appl. No.: 08/990,447

[22] Filed: Dec. 15, 1997

Related U.S. Application Data

[63] Continuation of application No. PCT/JP97/01321, Apr. 17, 1997.

[30] Foreign Application Priority Data

Apr. 18, 1996 [JP] Japan ................................. 8-097036
Apr. 18, 1996 [JP] Japan ................................. 8-097045

[51] Int. Cl.[7] .................................................. H01C 7/00
[52] U.S. Cl. ............................................ 338/34; 338/35
[58] Field of Search ...................... 338/34, 35; 73/31.06, 73/23; 438/567, 643, 648; 257/33, 34, 35, 39, 30

[56] References Cited

U.S. PATENT DOCUMENTS 4,313,338  2/1982  Abe et al. ..................................... 73/23
4,352,286  10/1982  Nakatani et al. ............................ 73/23

FOREIGN PATENT DOCUMENTS

| 0046498 | 4/1977 | Japan . |
| 52-60695 | 5/1977 | Japan . |
| 56-33535 | 4/1981 | Japan . |
| 1213562 | 8/1989 | Japan . |
| 6-258270 | 9/1994 | Japan . |
| 7-140100 | 6/1995 | Japan . |

OTHER PUBLICATIONS

Dictionary of Physics and Chemistry, 4th Edition (see Appln. p. 4), p. 761.
English Translation of JP–06258270 published Sep. 16, 1994.

*Primary Examiner*—Michael L. Gellner
*Assistant Examiner*—Richard K. Lee
*Attorney, Agent, or Firm*—Pillsbury Madison & Sutro, LLP

[57] ABSTRACT

In a gas sensor which uses CuO as a p-type semiconductor, by adding $Na_2CO_3$ in excess of 1 wt % relative to CuO, sensitivity to gases such as $H_2$, NO, $NO_2$ and $SO_2$ is suppressed, whereby selectivity for CO is increased. Sensitivity to $CO_2$ can also be obtained. In addition, by adding a sodium salt of tungstic acid or molybdic acid, $CO_2$ sensitivity can be made lower than the CO sensitivity, and CO gas in the exhaust gases discharged from gas-fired water heaters or other combustion equipment can be selectively detected. It is therefore possible to detect incomplete combustion.

22 Claims, 23 Drawing Sheets

Plan View of Second Embodiment

Plan View of First Embodiment

Side View of First Embodiment

Rear Plan View of First Embodiment

Plan View of Second Embodiment

Sectional View of Second Embodiment

Mode of use

Mode of use

Mode of use

Mode of use

Apparatus for Measuring Sensitivity

Example of Measurement Results (prior art)

Gas Sensor used for Measurements

Side View

Electrode

Lead Wire

View Facing One of the Electrodes

Measurement Example 1

Measurement Example 2

Measurement Example 3

Measurement Example 6

Measurement Example 6

Measurement Example 7

CO concentration dependence

Measurement Example 8 hydrogen concentration deperdence

Measurement Example 8 oxygen concentration dependence  Measurement Example 8 water vapor concentration dependence  Measurement Example 8

Measurement Example 8

Measurement Example 9

Measurement Example 11

Measurement Example 12

Measurement Example 13

Measurement Example 14

Measurement Example 15

Measurement Example 16

GAS SENSORS AND METHODS OF MANUFACTURING THE SAME

This is a Continuation of International Appln. No. PCT/JP97/01321 filed Apr. 17, 1997 which designated the U.S.

TECHNICAL FIELD

The present invention is utilized for the detection of gases contained in trace amounts in gaseous mixtures.

BACKGROUND ART

Sensors that make use of ceramic semiconductor materials to detect gases present in air have been known for some time. Whereas hitherto only sensors utilizing reactions involving n-type ceramic semiconductors were known, the inventors associated with the present application have discovered that gases can be detected using high-purity CuO, which is a p-type semiconductor. They have previously filed a patent application for this, which application will hereinafter be referred to as "the prior application." This prior application was laid open to public inspection as Japanese Kokai Patent 6-258270. In the gas sensor disclosed in this prior application, at least 99 wt % of the semiconductor component contributing to conductivity in the sintered product was CuO, and the amount of additive was no more than 1 wt %. It was also disclosed in the prior application that CO sensitivity is increased by adding an alkaline metal compound as this additive which is present at no more than 1 wt %.

However, although CO sensitivity was increased by adding an alkali metal compound to the high-purity CuO, the CO sensitivity thus obtained was only about twice the sensitivity to the same concentration of $H_2$ for example. A further consideration is that recent research on the connection between global warming and $CO_2$ gas has highlighted the need for a gas sensor capable of measuring $CO_2$ gas concentrations.

Meanwhile, detection of gases in exhaust gases differs from detection in air in that the partial pressure of oxygen varies, and $CO_2$ concentration and water vapor partial pressure vary according to the state of combustion. Under such conditions there are no sensors with high enough sensitivity to CO alone that they can be used for CO detection without some modification. For example, a gas sensor comprising CuO with addition of $Na_2CO_3$ is sensitive to $CO_2$ as well, and at the $CO_2$ concentrations present in exhaust gas from gas-fired water heaters, its sensitivity to $CO_2$ is close to its sensitivity to CO at the CO concentrations which have to be detected to give warning of a dangerous amount of CO. This means that selective detection of CO will sometimes be unsuccessful.

For example, in experiments performed by the present inventors, it was found that at a $CO_2$ concentration of 5.5% an experimental gas sensor comprising CuO with addition of $Na_2CO_3$ gave about the same detection output for $CO_2$ as the output in response to the approximately 2000–4000 ppm of CO which was generated during incomplete combustion. Given that both $CO_2$ and CO are present in exhaust gas during incomplete combustion, and that even during normal combustion $CO_2$ is generated at concentrations sufficiently large to be expressed in percent rather than ppm, it will be seen that such high sensitivity to $CO_2$ is unsuitable for selective detection of CO.

It is an object of the present invention to solve such problems by providing gas sensors capable of selective detection of CO and $CO_2$; gas sensors in which the $CO_2$ sensitivity has been made lower than the CO sensitivity; and manufacturing methods for these sensors.

DISCLOSURE OF INVENTION

According to a first aspect, the present invention is a gas sensor capable of selective detection of CO and $CO_2$, and having a p-type member formed from a p-type semiconductor the main constituent of which is CuO, and two electrodes which are connected to this p-type member, said electrodes serving to extract changes in electrical characteristics resulting from the presence of a gas to be detected, wherein the p-type semiconductor contains, as an additive, $Na_2CO_3$ in excess of 1 wt % relative to CuO.

The increase in CO gas selectivity due to adding a sodium compound to CuO, which is a p-type semiconductor, is the same as disclosed in the prior application. Nevertheless, when the prior application was filed it was thought that gas detection by means of a structure in which electrodes are attached to a p-type semiconductor consisting mainly of CuO was possible only if high-purity CuO was used, i.e., CuO in which additive-derived semiconductor constituents other than CuO amount to no more than 1 wt %.

However, subsequent research has revealed that gas detection is still possible when the amount of additive is increased. Sensitivity to gases such as $H_2$, NO, $NO_2$ and $SO_2$ can be kept low, and selectivity for CO increased, by adding $Na_2CO_3$ in excess of 1 wt %. It was also found that sensitivity to $CO_2$ can be obtained as well. Such characteristics are maintained even when the amount of $Na_2CO_3$ added is increased to 40 wt %, but if the amount added is increased further, the sintered product tends to lose its molded shape and therefore cannot be used as a sensor. Given the strength required to withstand use as a sensor, it is preferable for no more than 20 wt % of $Na_2CO_3$ to be added.

According to a second aspect, the present invention is a method for manufacturing such a gas sensor by forming a member with electrical characteristics which change in accordance with the presence of a gas to be detected, said member being formed by adding to powdered CuO a sodium compound which will become $Na_2CO_3$ as a result of firing, and then molding and firing, wherein the amount of sodium compound added results in the $Na_2CO_3$ content exceeding 1 wt % of the CuO.

The sintered mass can be used as a gas sensor either just as it is, or after machining to a suitable size. Alternatively, it can be formed as a thick film. Namely, a gas sensor can be obtained by first of all manufacturing a paste whereof the main solid constituents are powdered CuO and a sodium compound additive which becomes $Na_2CO_3$ as a result of firing, then printing this paste onto a substrate and firing. A thick film can also be formed by grinding the sintered mass described above and using this as the raw material.

The powdered CuO used as the raw material preferably has primary particles with a specific surface area of at least 2 $m^2/g$, and more preferably of at least 20 $m^2/g$. A specific surface area of at least 2 $m^2/g$ is equivalent to a particle size of 1 $\mu m$ or less, while a specific surface area of at least 20 $m^2/g$ is equivalent to a particle size of 0.25 $\mu m$ or less. In experiments performed by the inventors, when CuO with a specific surface area of less than 2 $m^2/g$ was used, subsequent sintering did not go to completion and the sintered product obtained ended up being easily broken. It is therefore thought that a practical gas sensor cannot be obtained using CuO with such a small specific surface area.

The maximum temperature during firing is preferably at least 400° C., and preferably no more than 860° C. A temperature of at least 500° C. and no more than 700° C. is particularly desirable. In experiments performed by the inventors, when the firing temperature was lower than 400° C., sintering did not go to completion and the sintered product obtained was easily broken when handled. It was also found that good properties were not obtained when firing was carried out at temperatures exceeding 860° C. This may be because there is a relation between the temperature at which $Na_2CO_3$ loses $CO_2$ and the temperature at which $Na_2CO_3$ decomposes (see for example "Dictionary of Physics and Chemistry" published by Iwanami Shoten, 4th edition, p.761).

A variety of methods can be used for adding $Na_2CO_3$. For example, $Na_2CO_3$ can be dissolved in water, CuO powder dispersed in the resulting solution, and then the water removed by drying. Alternatively, $NaHCO_3$ can be added and then thermally decomposed in the firing process.

According to a third aspect, the present invention is a gas sensor in which the $CO_2$ sensitivity has been made lower than the CO sensitivity, said gas sensor having a p-type member formed from a p-type semiconductor the main constituent of which is CuO and to which a sodium compound has been added, and two electrodes which are connected to this p-type member, said electrodes serving to extract changes in electrical characteristics resulting from the presence of a gas to be detected, wherein the sodium salt of at least one acid selected from the group comprising tungstic acid and molybdic acid is included as the sodium compound.

According to research by the present inventors, if the sodium salt of tungstic acid or molybdic acid is added, $CO_2$ sensitivity decreases relative to CO sensitivity. By utilizing such materials in gas sensors, CO gas can be selectively detected in the exhaust gas discharged by gas-fired water heaters and other combustion equipment, and incomplete combustion can be detected.

The content of the sodium compound is preferably from 0.5 to 23 wt % as tungsten relative to CuO when a sodium salt of tungstic acid is used, and preferably 0.4 to 16 wt % as molybdenum relative to CuO when a sodium salt of molybdic acid is used.

According to a fourth aspect, the present invention is a method for manufacturing such gas sensors by forming a member with electrical characteristics which change in accordance with the presence of a gas to be detected, said member being formed by adding a sodium compound to CuO and then molding and firing, wherein a substance which will become a sodium salt of tungstic acid or a sodium salt of molybdic acid upon firing is added as the sodium compound.

In experiments performed by the present inventors, when $Na_2WO_4.2H_2O$ or $Na_2MoO_4.2H_2O$ was used as the added substance, good results were obtained at additions of 1 to 40 wt % relative to CuO. These additions are equivalent to 0.5 to 23 wt % of tungsten relative to CuO, and 0.4 to 16 wt % of molybdenum relative to CuO. If the amount of addition exceeded 40 wt %, the sintered product did not maintain a solid shape and could not be used as a sensor. In particular, if the sintered product is used as a mass, then for both $Na_2WO_4.2H_2O$ and $Na_2MoO_4.2H_2O$ an addition of 20 wt % ensured that it could readily be handled without breaking.

In these cases as well it is preferable for the maximum temperature during firing to be at least 400° C. and no more than 860° C. In experiments by the present inventors, the sintered product could be readily handled without breaking if the maximum temperature during firing was at least 500° C. In addition, sensitivity to co-present gases could be kept low by ensuring that the maximum temperature during firing was at least 500° C. and no more than 850° C.

BEST MODE FOR CARRYING OUT THE INVENTION

Figure 1:
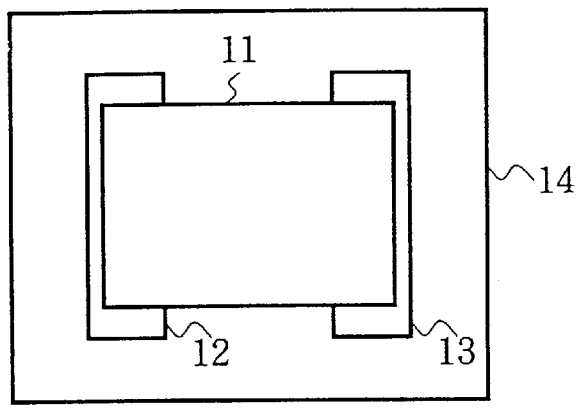
FIG. 1 to FIG. 3 show a first embodiment of the present invention, with FIG. 1 being a plan view, FIG. 2 a side view and FIG. 3 a rear plan view.
Figure 2:
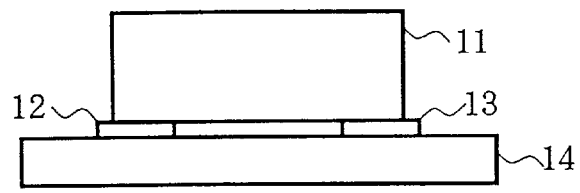
Figure 3:
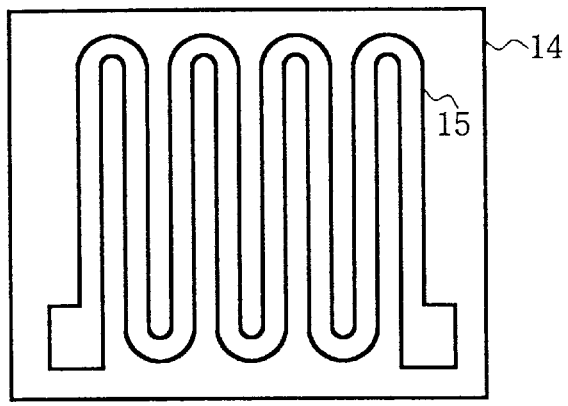

FIG. 1 to FIG. 3 show a first embodiment of a gas sensor according to the present invention. FIG. 1 is a plan view, FIG. 2 a side view and FIG. 3 a rear plan view. This gas sensor has a construction in which Au electrodes 12 and 13 are formed on ceramic substrate 14, and p-type member 11 comprising a sintered mass is in contact with these Au electrodes 12 and 13. P-type member 11 is formed from a p-type semiconductor whereof the main constituent is CuO, and the two Au electrodes 12 and 13 are connected to this p-type member 11 so that they can extract changes in electrical characteristics resulting from the presence of a gas to be detected. Heater 15 for heating can be provided on the rear of ceramic substrate 14 so that this gas sensor can be heated. When operating, a voltage is applied between Au electrodes 12 and 13, and changes in voltage or current, or in voltage and current, between Au electrodes 12 and 13 due to the presence of a gas to be detected are monitored.

A p-type semiconductor containing, as an additive, $Na_2CO_3$ in excess of 1 wt % relative to CuO is used as p-type member 11. Alternatively, a p-type semiconductor containing the sodium salt of at least one acid selected from the group comprising tungstic acid and molybdic acid is used as p-type member 11.

The p-type semiconductor containing $Na_2CO_3$ as an additive is obtained by adding to powdered CuO a sodium compound which will become $Na_2CO_3$ as a result of firing, and then molding and firing this. The CuO used as the raw material has primary particles with a specific surface area of at least 2 $m^2$/g and preferably of at least 20 $m^2$/g, and with a particle size of no more than 1 μm and preferably of no more than 0.25 μm. The amount of addition of the sodium compound is at least 1 wt % as $Na_2CO_3$ relative to CuO, and preferably at least 1 wt % and no more than 40 wt %, and more preferably still at least 1 wt % and no more than 20 wt %. The maximum temperature during firing is at least 400° C. and preferably no more than 860° C., and more preferably still at least 500° C. and no more than 700° C. Bulk density can be controlled and CO selectivity increased by appropriate selection of the particle shape of the CuO raw material powder, and of the maximum firing temperature.

The p-type semiconductor containing a sodium salt of tungstic acid or molybdic acid as an additive is obtained in similar manner by mixing with CuO a sodium compound of the sort that such an additive will be obtained by firing, and then molding and firing this.

Figure 4:
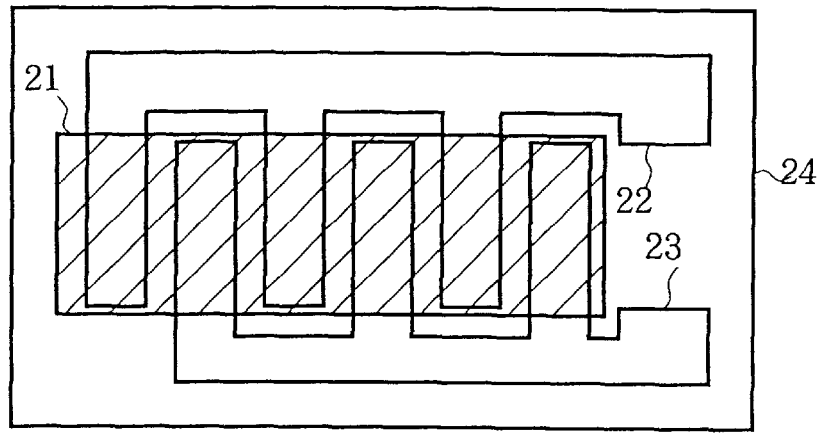
FIG. 4 and FIG. 5 show a second embodiment of the present invention, with FIG. 4 being a plan view and FIG. 5 a sectional view.
Figure 5:
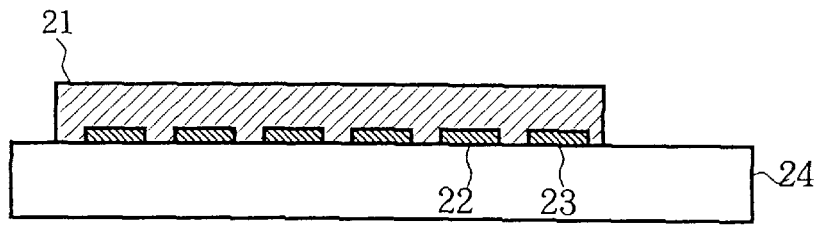

FIG. 4 and FIG. 5 show a second embodiment of a gas sensor according to the present invention. FIG. 4 is a plane view, and FIG. 5 is a sectional view.

This gas sensor comprises interdigitated electrodes 22 and 23 which are formed on ceramic substrate 24, and p-type member 21 which has been formed as a thick film over these electrodes. P-type member 21 is formed by firstly printing a paste so as to be in contact with interdigitated electrodes 22 and 23, said paste having as its main solid constituents powdered CuO and an additive, the additive being either a sodium compound which becomes $Na_2CO_3$ as a result of firing, or a sodium compound which becomes a sodium salt of tungstic acid or molybdic acid as a result of firing. This paste is then fired. Although not illustrated, as in the first embodiment a heater can be provided on the rear surface of ceramic substrate 24 in order to heat this gas sensor. It is also possible to form a thick film in the same manner as in the first embodiment, by using as the raw material the product obtained by grinding the sintered mass. Alternatively, a thick film can be formed by mixing the sodium compound with powdered CuO, dispersing the mixture in an organic solvent, using screen printing or other method to print the paste obtained, and then firing this printed paste.

Figure 6:
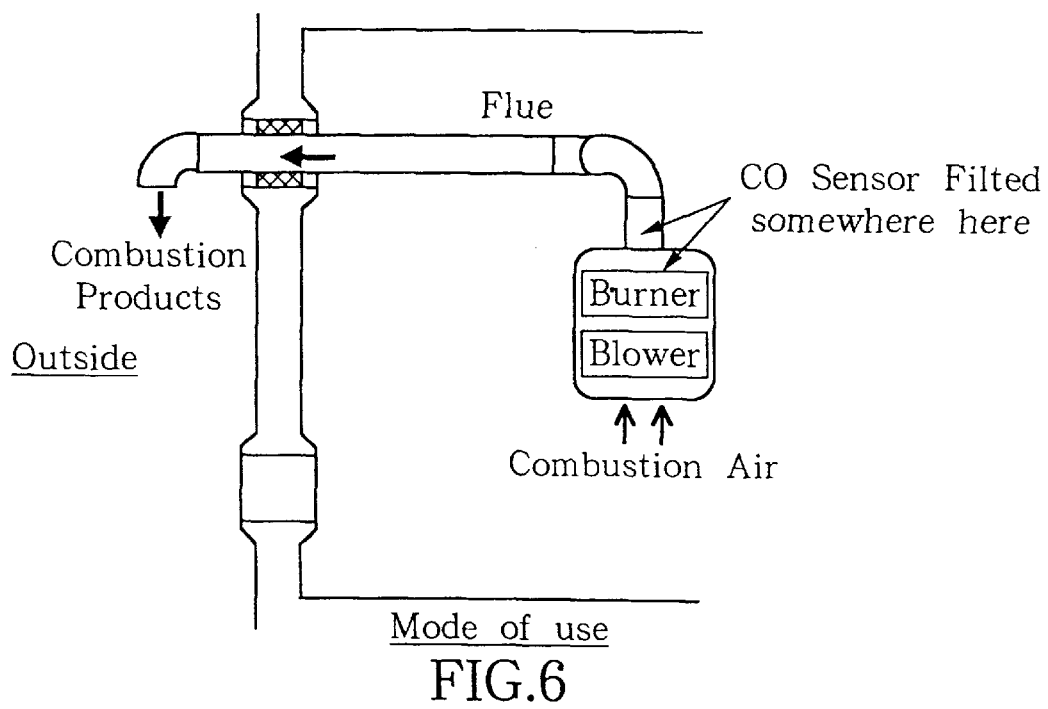
FIG. 6 to FIG. 9 show several ways for utilizing a gas sensor in which a sodium salt of tungstic acid or molybdic acid has been added to CuO.
Figure 7:
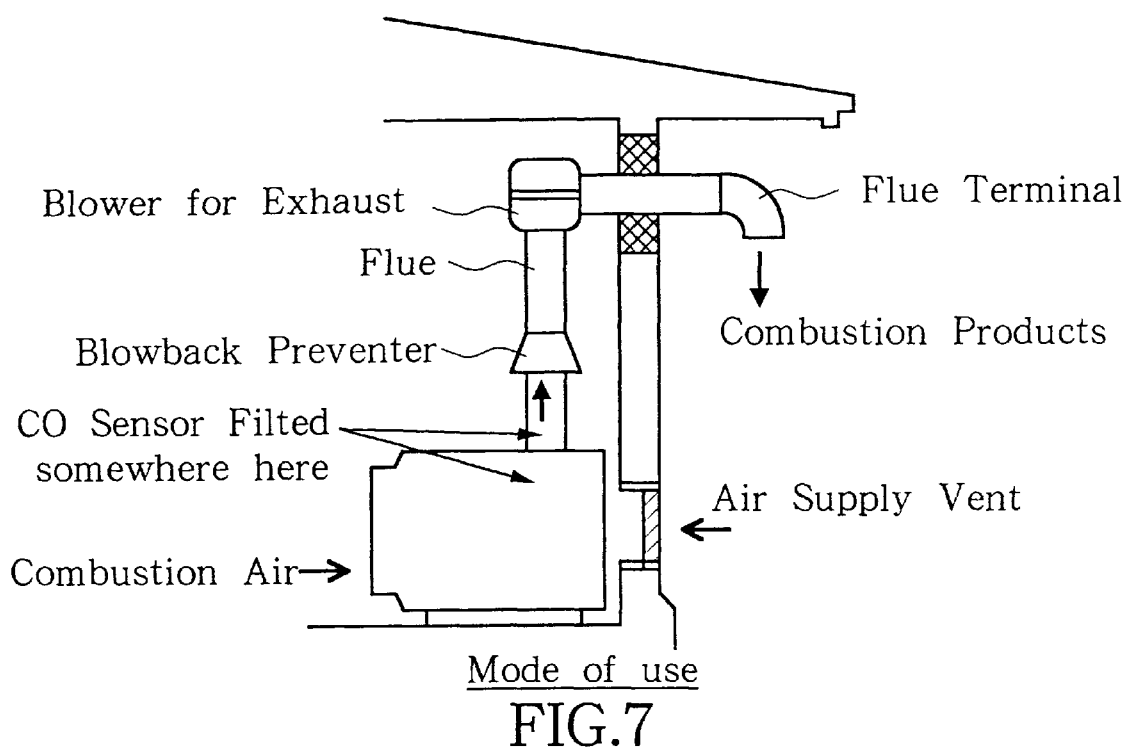
Figure 8:
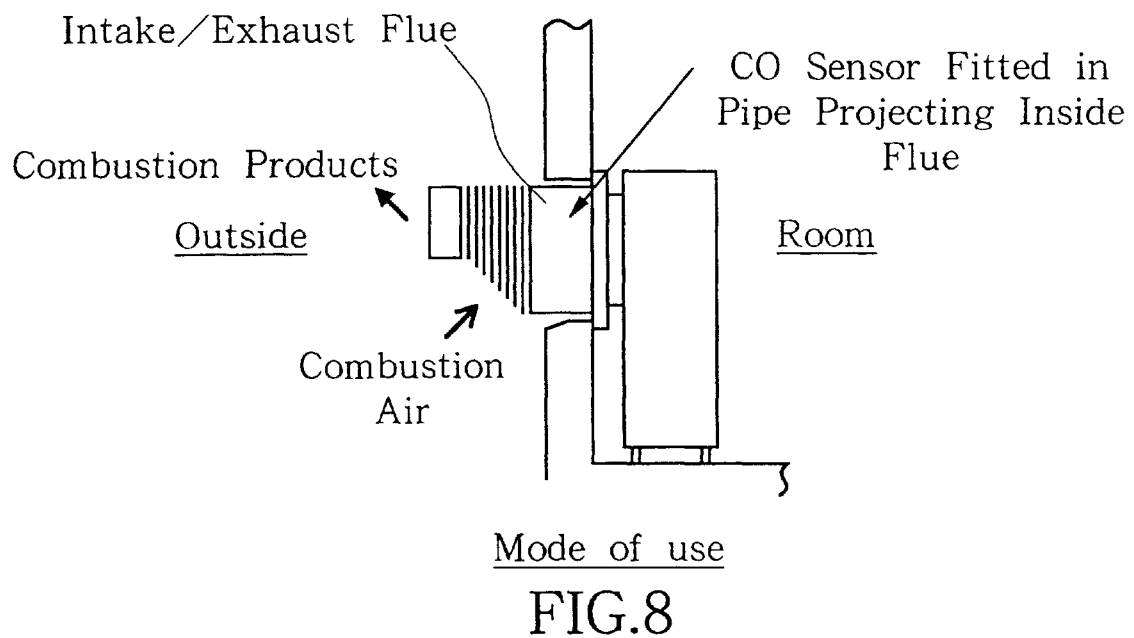
Figure 9:
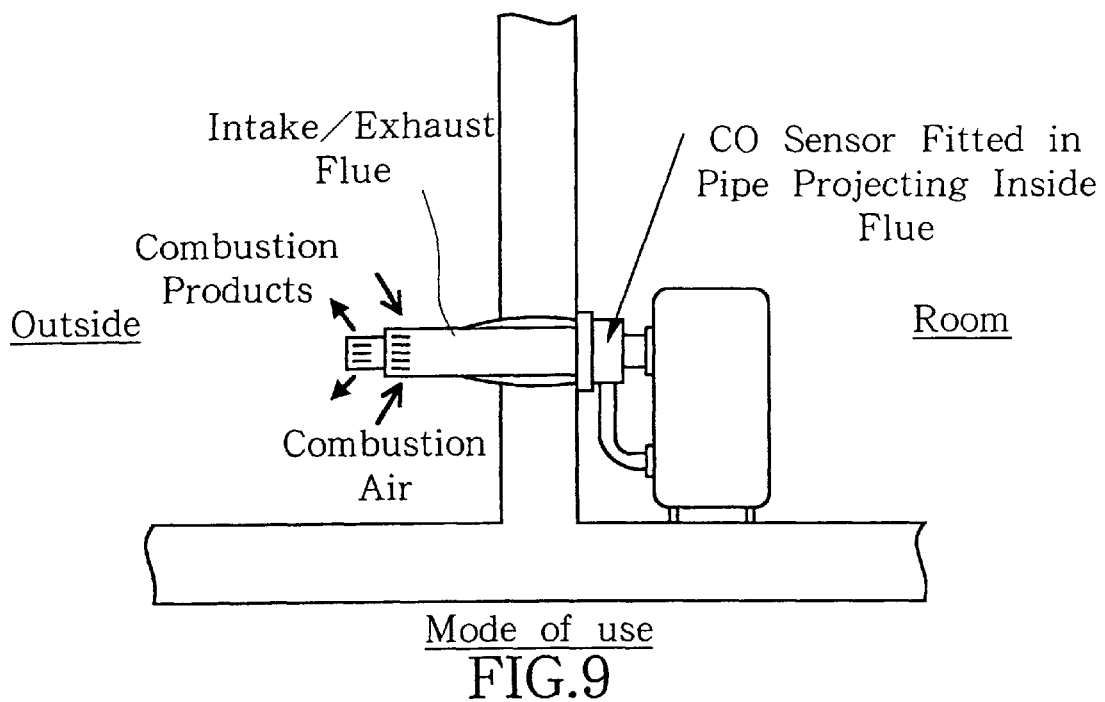

FIG. 6 to FIG. 9 show several ways for utilizing a gas sensor in which a sodium salt of tungstic acid or molybdic acid has been added to CuO. A gas sensor in which $Na_2CO_3$ has been added to CuO is capable of selective detection of CO and $CO_2$, and it is assumed that such sensors will mainly be used in the air. As opposed to this, because a gas sensor in which a sodium salt of tungstic acid or molybdic acid has been added to CuO has a $CO_2$ sensitivity which is relatively low compared with its CO sensitivity, and is capable of selective detection of CO gas in the exhaust gases discharged from combustion equipment, its utilization will involve being fitted inside, or to the exhaust system of, various types of combustion equipment. FIG. 6 shows forced draft type combustion equipment which uses a blower to feed room air to the burner and to discharge exhaust gas to the outside. FIG. 7 shows forced exhaust type combustion equipment which uses air taken in from the room and from outside for combustion, and discharges exhaust gases to the outside by means of a blower. FIG. 8 shows natural feed and exhaust type combustion equipment which takes in outside air for combustion and discharges the exhaust gases to the outside. FIG. 9 shows forced feed and exhaust type combustion equipment which takes in outside air and forcibly discharges exhaust gases.

The results of measurements of experimental gas sensors will now be explained.

Figure 10:
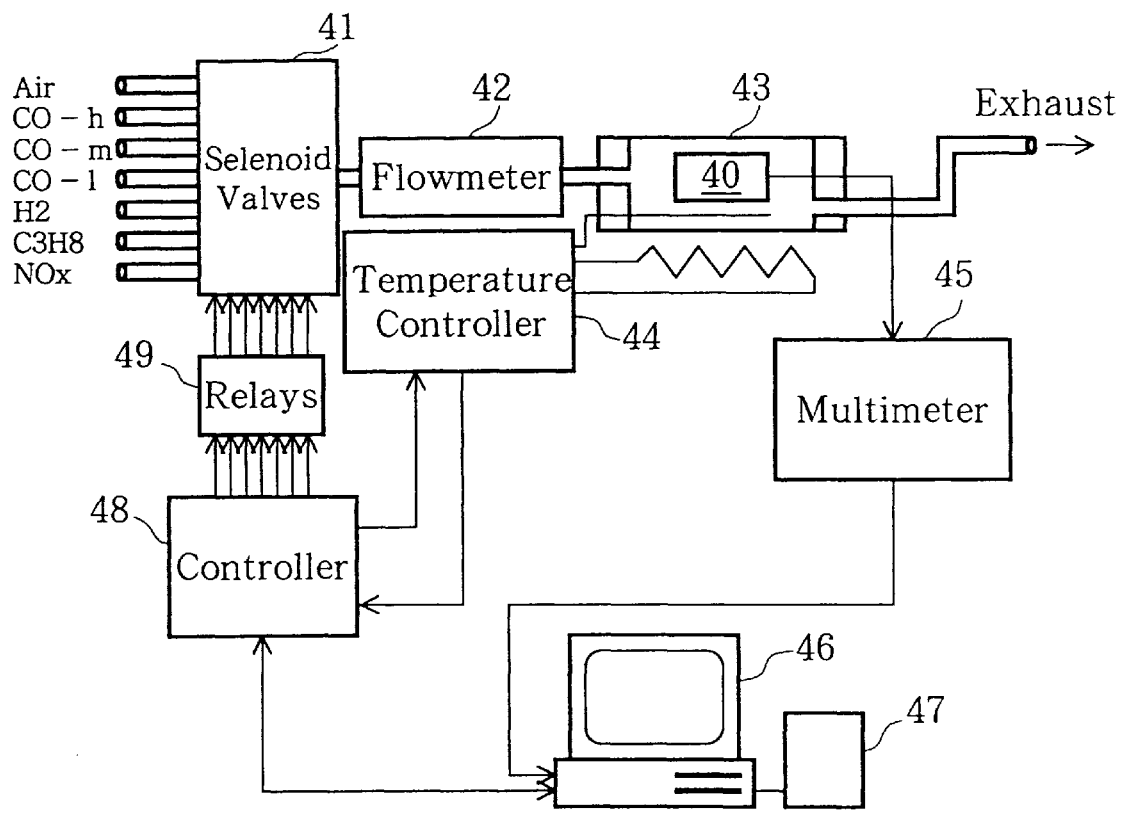
FIG. 10 shows the configuration of apparatus for measuring sensitivity to gases.

FIG. 10 shows the configuration of apparatus for measuring sensitivity to gases. This measuring apparatus is operated as follows. Gas sensor 40 to be tested is placed inside quartz tube 43 and a flow of air plus a gas to be detected, such as CO or $H_2$, is passed into this quartz tube 43 via solenoid valves 41 and mass flowmeter 42. The temperature of the gas flow is controlled by temperature controller 44. The voltage applied to gas sensor 40 and the current flowing through it are measured by multimeter 45, and the measured values are processed by personal computer 46 and stored in external storage device 47. Solenoid valves 41 are configured to be capable of selecting the gas to be detected, adding it to air, and supplying the mixture to quartz tube 43. They are operated by control signals supplied from controller 48 via relays 49. When personal computer 46 has acquired the value of the current detected by multimeter 45, after a suitable time has elapsed it outputs to controller 48 a control signal for switching over the gas being supplied. The operating temperature of gas sensor 40 being measured is set to 230–260° C. If a heater has been provided on gas sensor 40, this operating temperature is controlled by this heater. If a heater is not provided, the operating temperature is controlled from outside quartz tube 43.

Figure 11:
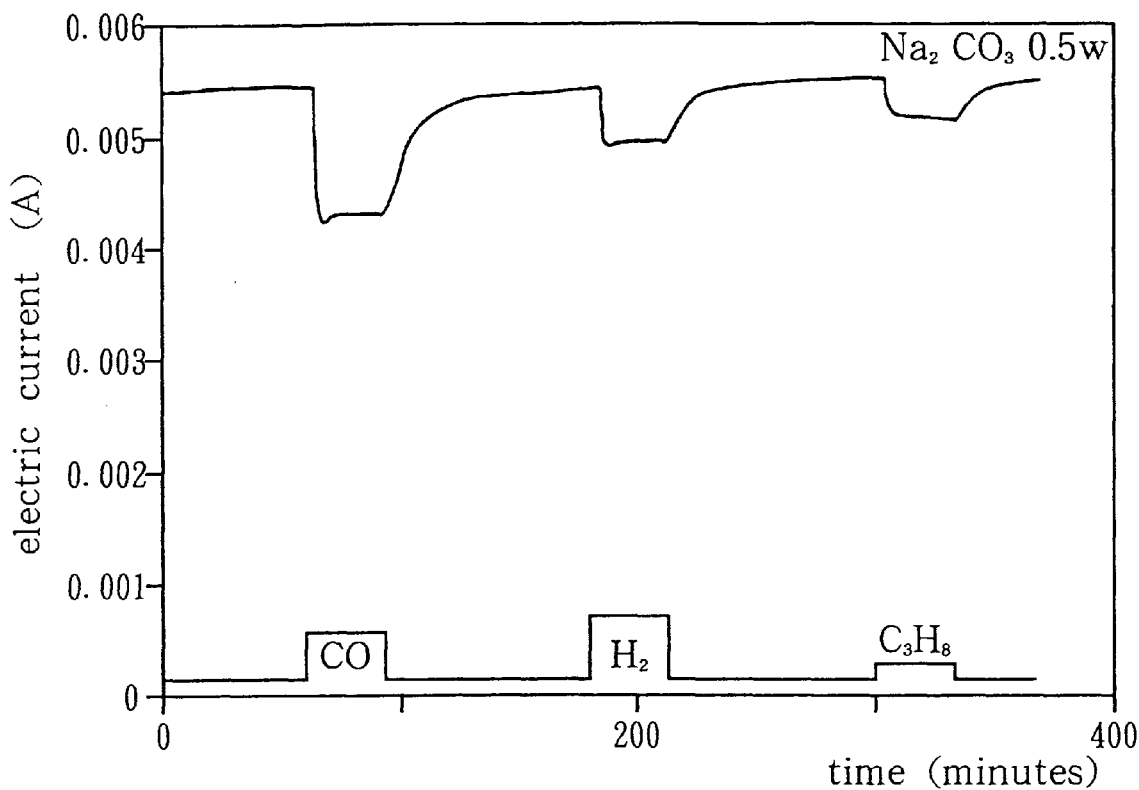
FIG. 11 shows, for reference, an example of measurement results.

FIG. 11 shows an example of the results of measurements obtained by multimeter 45. These results are the same as those shown in FIG. 6 of the prior application. In this example, a sintered mass comprising 0.5 wt % addition of $Na_2CO_3$ to CuO was maintained at 260° C., a fixed voltage applied, and CO, $H_2$ and $C_3H_8$ supplied as test gases to be detected. In each case, the supplied gas flow consisted of 4000 ppm of the test gas in air. When each test gas was introduced, a change in electric current was observed. The supply of the test gas was then discontinued, and after the current had stabilized again, the next test gas for detection was introduced. The larger the current fluctuation, the higher the sensitivity to the gas being detected.

However, although the difference in sensitivity of a given gas sensor to each test gas can be indicated by comparing the sizes of the current fluctuations, comparisons cannot be made with other gas sensors. Accordingly, in the present specification the value defined as:

$[(R_{gas}/R_0)-1] \times 100$ is used to indicate sensitivity, where $R_0$ is resistance in air and $R_{gas}$ is resistance under a flow of the gas to be detected. Alternatively, the value defined as:

$[(R_{gas}/R_{base})-1] \times 100$ is used to indicate sensitivity when use in a location other than in the air is being considered. Here, $R_{base}$ is resistance in the base gas and $R_{gas}$ is resistance under a flow of the gas to be detected.

"Sensitivity ratio" will be used to express gas selectivity. For each test gas, this sensitivity ratio is the sensitivity to that gas normalized by the sensitivity to a particular test gas. For a given gas sensor, this sensitivity ratio coincides with the ratio of current change at a particular voltage.

MEASUREMENT EXAMPLE 1

Figure 12:
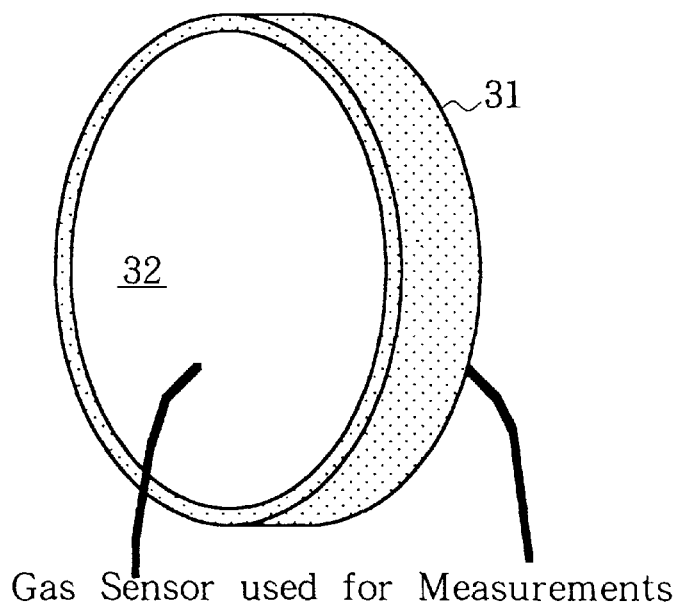
FIG. 12 to FIG. 14 show a gas sensor used for measurements, with FIG. 12 being a perspective view, FIG. 13 a side view and FIG. 14 a view facing one of the electrodes.
Figure 13:
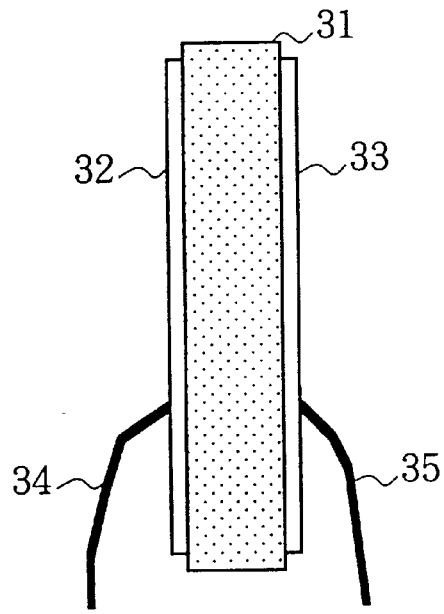
Figure 14:
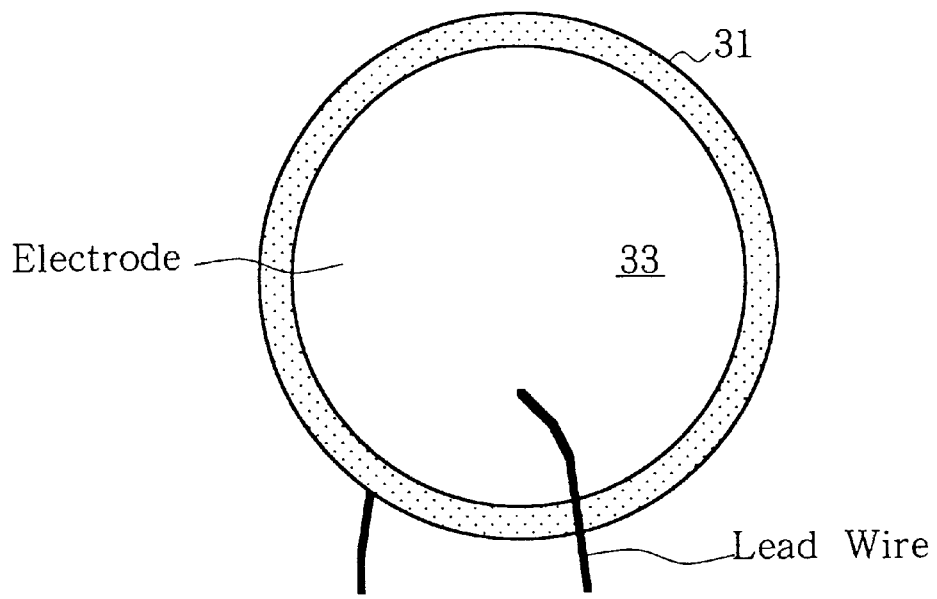

A gas sensor was fabricated by attaching electrodes to the sintered mass obtained by adding 10 wt % of $Na_2CO_3$ to CuO with primary particles having a specific surface area of 2.36 $m^2/g$, and then firing in air at 700° C. for 30 minutes. FIG. 12 to FIG. 14 show the structure of this gas sensor. FIG. 12 is a perspective view, FIG. 13 a side view, and FIG. 14 a view facing one of the electrodes. This gas sensor has a structure wherein sintered mass 31 is sandwiched between electrodes 32 and 33. Lead wires 34 and 35 are attached to electrodes 32 and 33 respectively. Mass 31 was 2.3 mm thick and its lateral surface area was approximately 50 $mm^2$.

Figure 15:
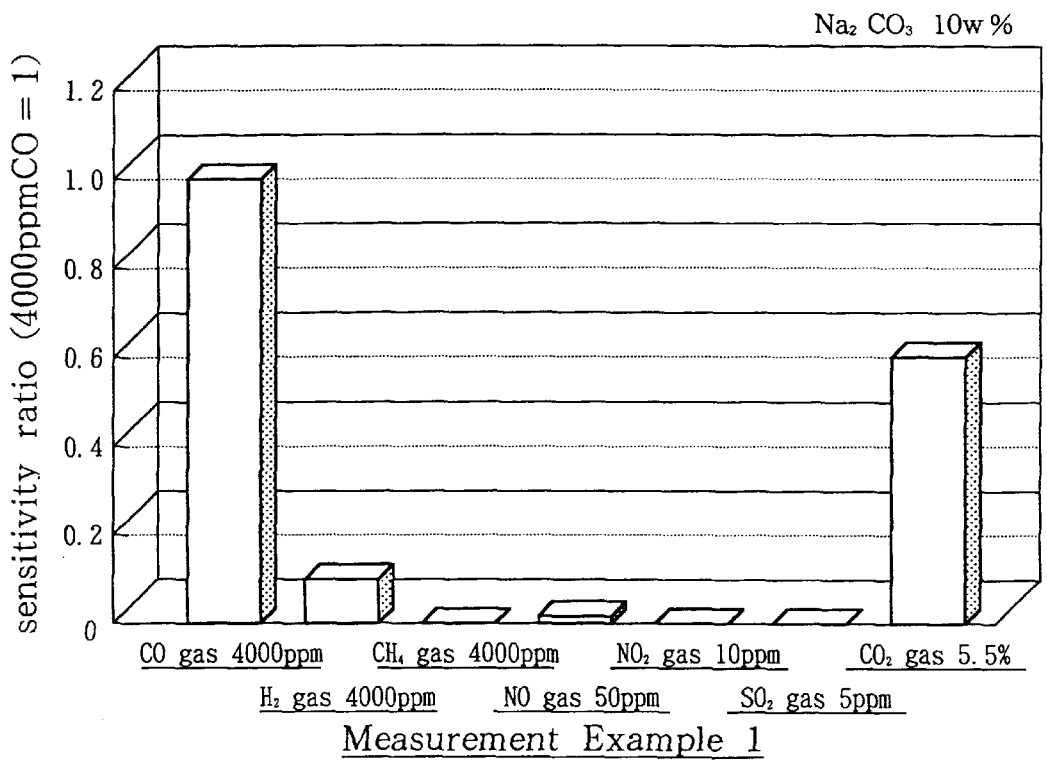
FIG. 15 gives an example of the results of measurements of sensitivity ratio for various gases.

FIG. 15 gives an example of the results of measurements of sensitivity ratio for various gases. For these measurements, 0.1 V was applied between electrodes 32 and 33. The sensitivity ratio for each test gas being detected was then obtained by taking the current change measured for 4000 ppm of CO as "1" and normalizing the current change measured for each test gas. In addition to CO, the following gases were tested: $H_2$, $CH_4$ (as a representative combustible gas which is present in air), NO and $NO_2$ as nitrogen oxides, $SO_2$ as a sulphur oxide, and $CO_2$. The following concentrations were used for the test gases: 4000 ppm for $H_2$ and $CH_4$; 50 ppm for NO; 10 ppm for $NO_2$; 5 ppm for $SO_2$; and 5.5% for $CO_2$. The base gas was air. It was found that the selectivity for CO was high, with the sensitivity ratio of $H_2$ relative to CO being approximately ⅒. It was also found that there was considerable sensitivity to $CO_2$ as well.

MEASUREMENT EXAMPLE 2

Figure 16:
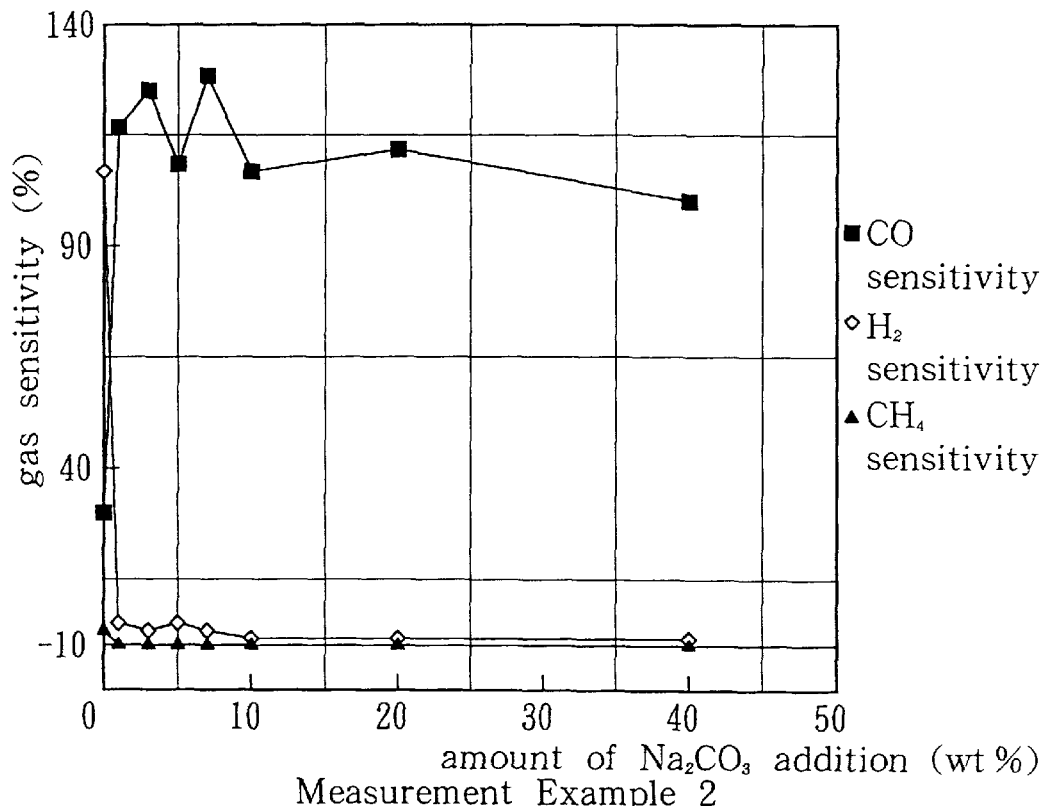
FIG. 16 gives measurements showing the dependence of gas sensitivity on the amount of $Na_2CO_3$ addition.

Gas sensors similar to that of Measurement Example 1 were fabricated with different amounts of $Na_2CO_3$ addition, and measurements made of variations in sensitivity to CO, $H_2$ and $CH_4$. The results of these measurements are given in FIG. 16. When the amount of $Na_2CO_3$ addition exceeded 1 wt %, sensitivity to CO became high, but sensitivity to the other gases became very low.

MEASUREMENT EXAMPLE 3

Figure 17:
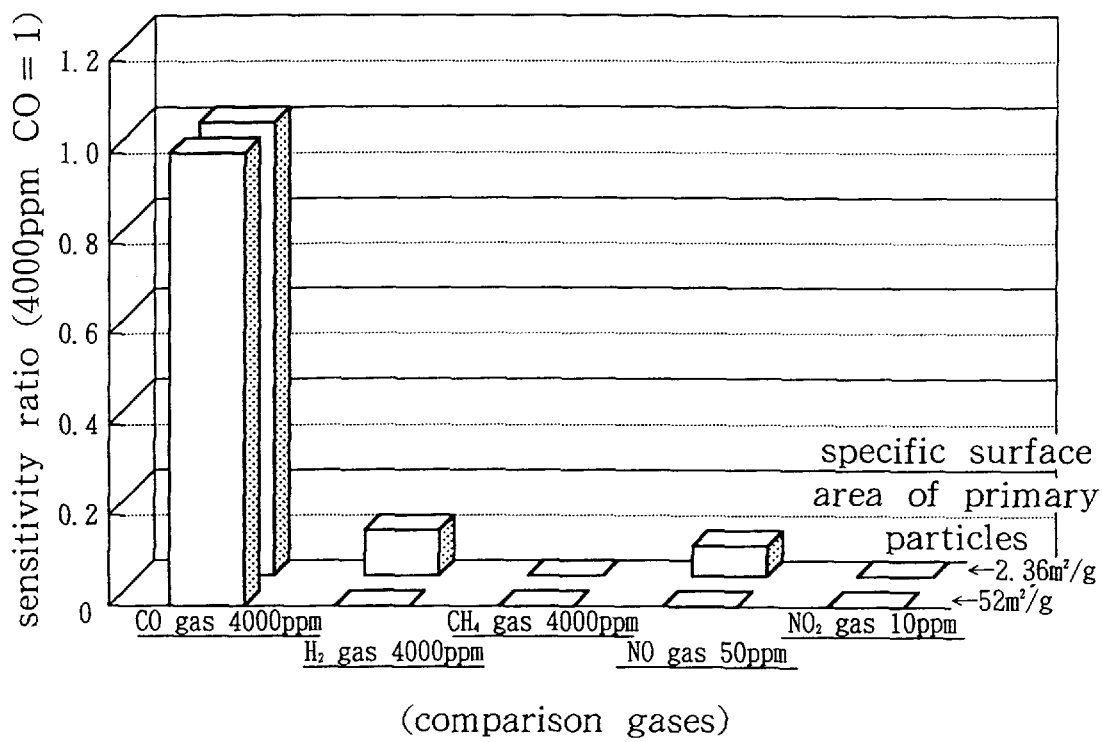
FIG. 17 shows the dependence of sensitivity ratio on the specific surface area of the CuO used as the raw material.

Gas sensors similar to that of Measurement Example 1 were fabricated using as the raw material CuO of different specific surface areas, and measurements made of variations in sensitivity ratio. An example of the results of these measurements is given in FIG. 17. This figure shows some of the measurement results already given in FIG. 15, side by side with the results of similar measurements made on a sintered mass fired under the same conditions but using as the raw material CuO having primary particles with a specific surface area of 52 $m^2/g$. It will be seen that although the additive and firing conditions were identical, the sensitivity ratios of both $H_2$ and NO were lower as a result of using as the raw material a CuO with a larger specific surface area.

Figure 18:
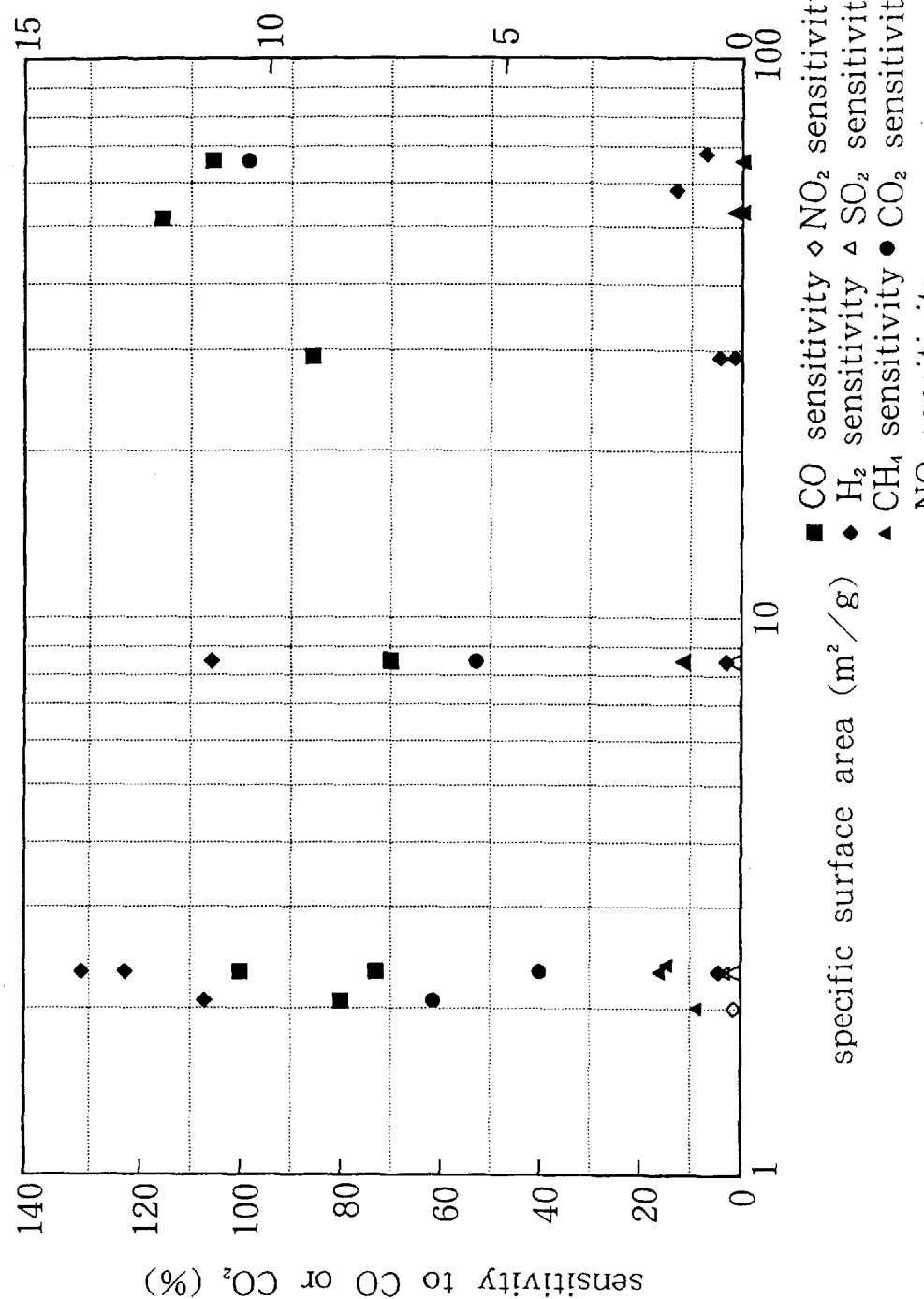
FIG. 18 shows the relation between sensitivity and the specific surface area of the CuO raw material.

FIG. 18 shows the relation between sensitivity and the specific surface area of the CuO raw material. CO, $H_2$, $CH_4$, NO, $NO_2$, $SO_2$ and $CO_2$ were used as the test gases, at concentrations of 4000 ppm, 4000 ppm, 4000 ppm, 50 ppm, 10 ppm, 5 ppm and 5.5%, respectively. The base gas was air. The vertical axis on the left-hand side of FIG. 18 shows the sensitivity to CO and $CO_2$, while the vertical axis on the right-hand side shows the sensitivity to the other co-present gases. Note that the scale of these two axes differs by a factor of approximately 10. It was found that the larger the specific surface area of the primary particles of powdered CuO used as the raw material, the lower the sensitivity to gases other than CO and $CO_2$. In particular, when the specific surface area exceeded 10–20 $m^2/g$, whereas the sensitivity to CO and $CO_2$ increased, the sensitivity to other gases such as $H_2$ underwent a marked decrease.

Figure 19:
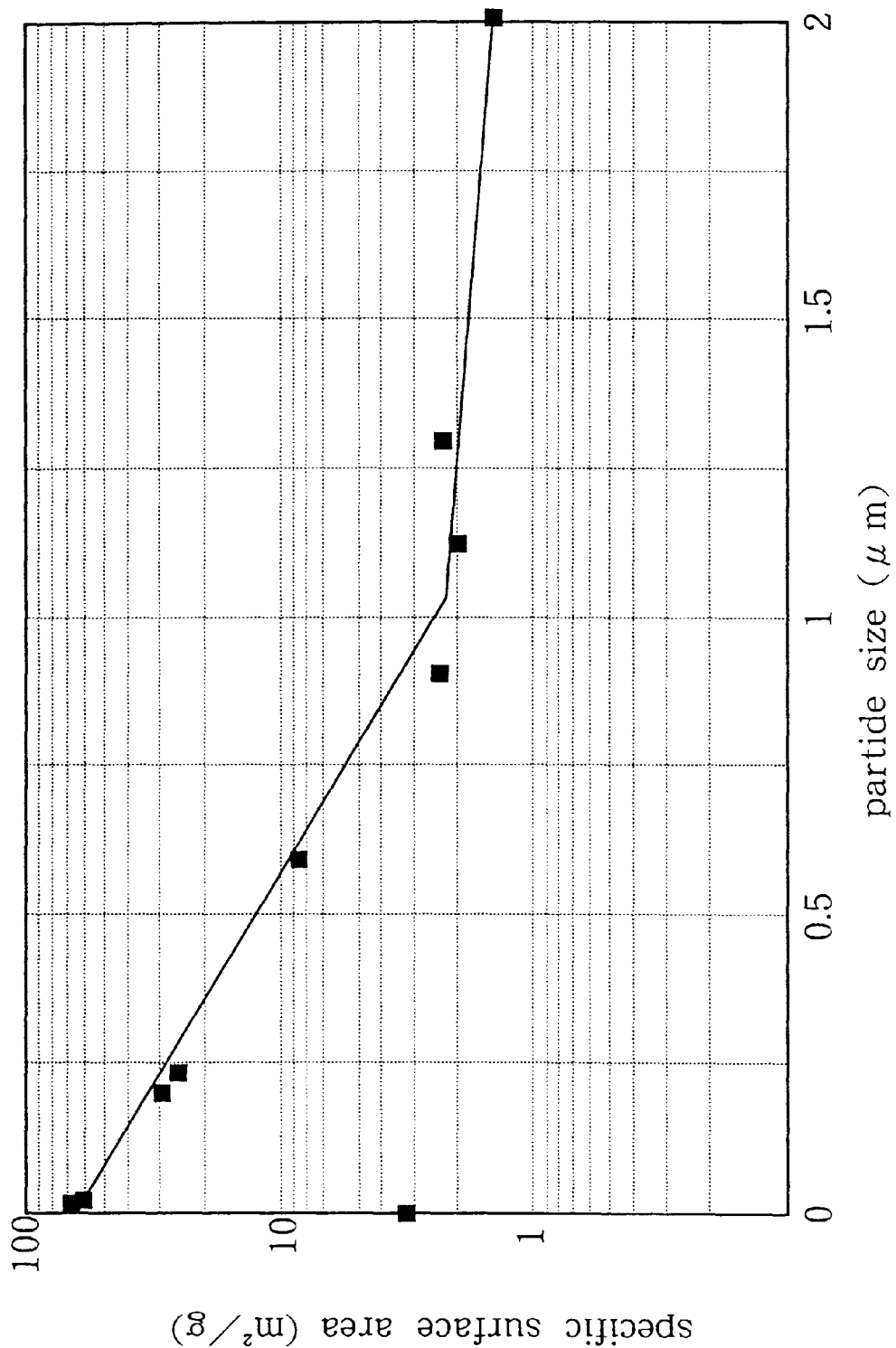
FIG. 19 shows the relation between particle size and specific surface area of CuO.

FIG. 19 shows the relation between particle size and specific surface area of CuO. A specific surface area of 2 $m^2/g$ or greater is equivalent to a particle size of less than about 1 μm.

MEASUREMENT EXAMPLE 4

Figure 20:
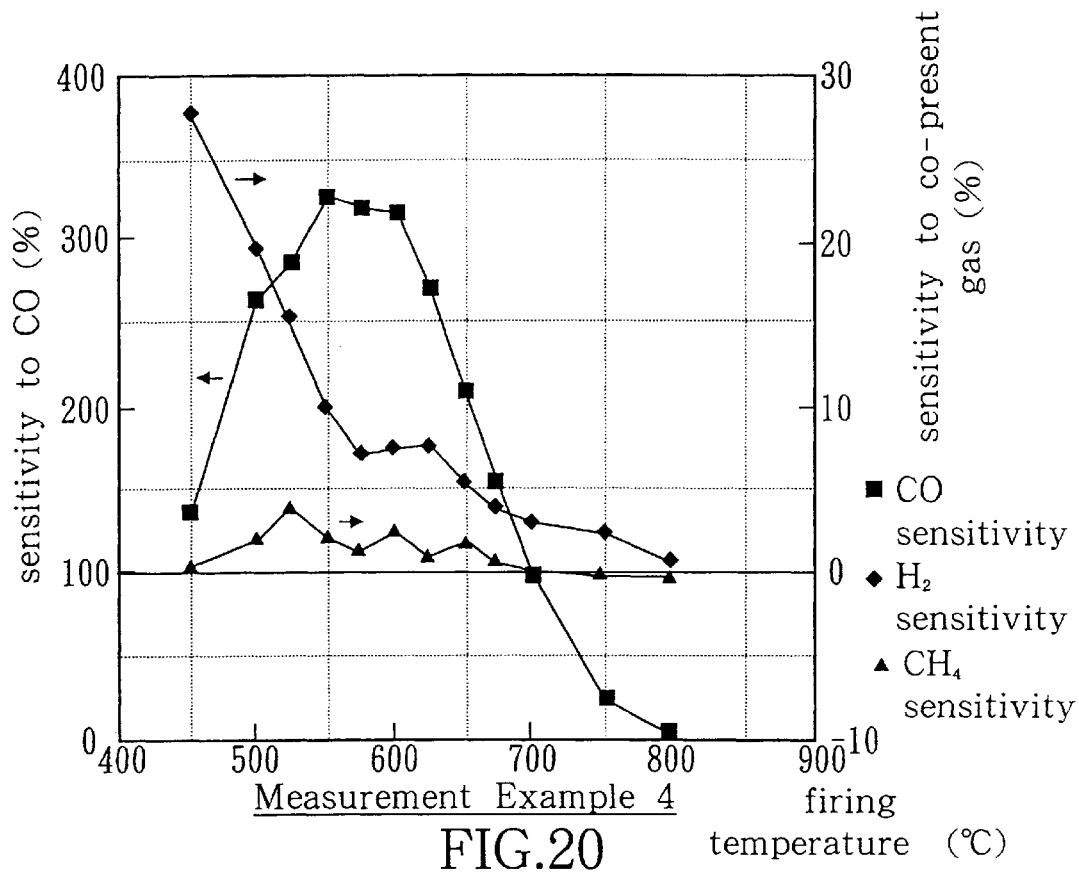
FIG. 20 shows the relation between firing temperature and sensitivity.

Gas sensors similar to that of Measurement Example 1 were fabricated using a variety of firing temperatures, and measurements made of variations in sensitivity ratio. An example of the results of these measurements is given in FIG. 20. The sensors were fired after 10 wt % of $Na_2CO_3$ had been added to CuO having primary particles with a specific surface area of 52 $m^2/g$. CO, $H_2$ and $CH_4$ were used as the test gases, in each case at a concentration of 4000 ppm. The base gas was air. The vertical axis on the left-hand side of FIG. 20 shows sensitivity to CO, while the vertical axis on the right-hand side shows sensitivity to the other co-present gas. When the firing temperature was 500° C. to 700° C., sensitivity to CO was high, and more than ten times the sensitivity to $H_2$. However, the sensitivity to CO decreased when the firing temperature was outside this temperature range.

Figure 21:
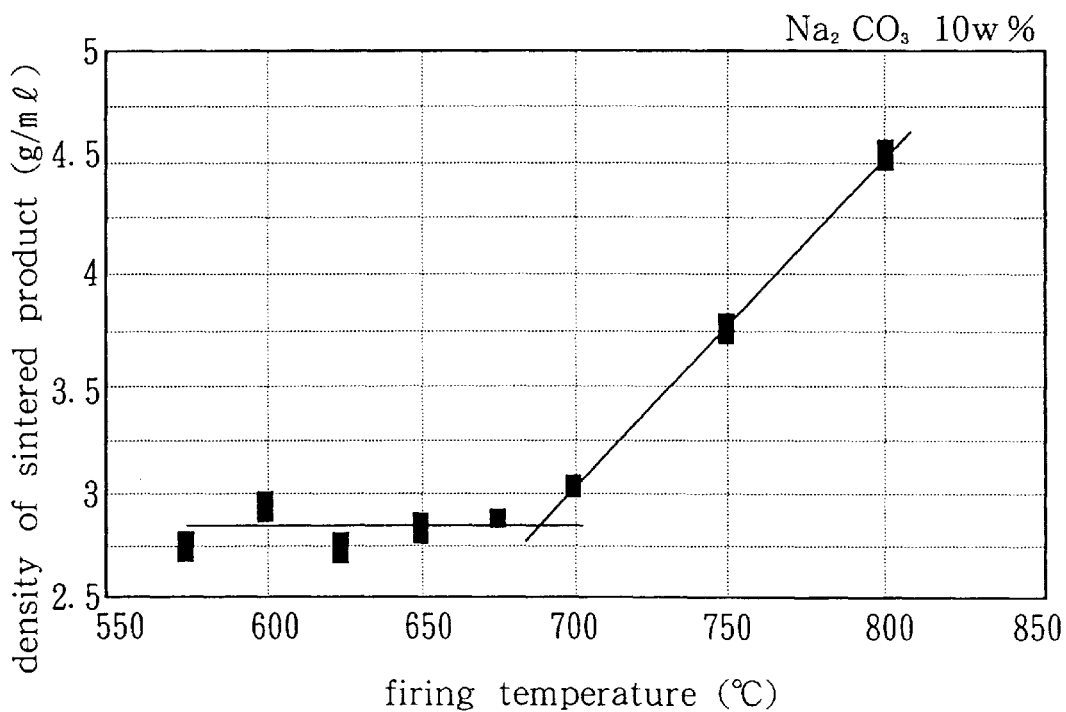
FIG. 21 shows the relation between firing temperature and the density of the sintered product obtained.

FIG. 21 shows the relation between firing temperature when 10 wt % of $Na_2CO_3$ was added to CuO, and the density of the sintered product obtained under these conditions. It will be seen that density increases abruptly when firing temperature exceeds 700° C.

MEASUREMENT EXAMPLE 5

A gas sensor with the construction shown in FIG. 1 to FIG. 3 was fabricated by cutting to shape, and attaching electrodes to, the sintered mass obtained by adding 8 wt % of $Na_2WO_4 \cdot 2H_2O$ to CuO and firing at a maximum temperature of 550° C. An alumina substrate was used as ceramic substrate 14.

Figure 22:
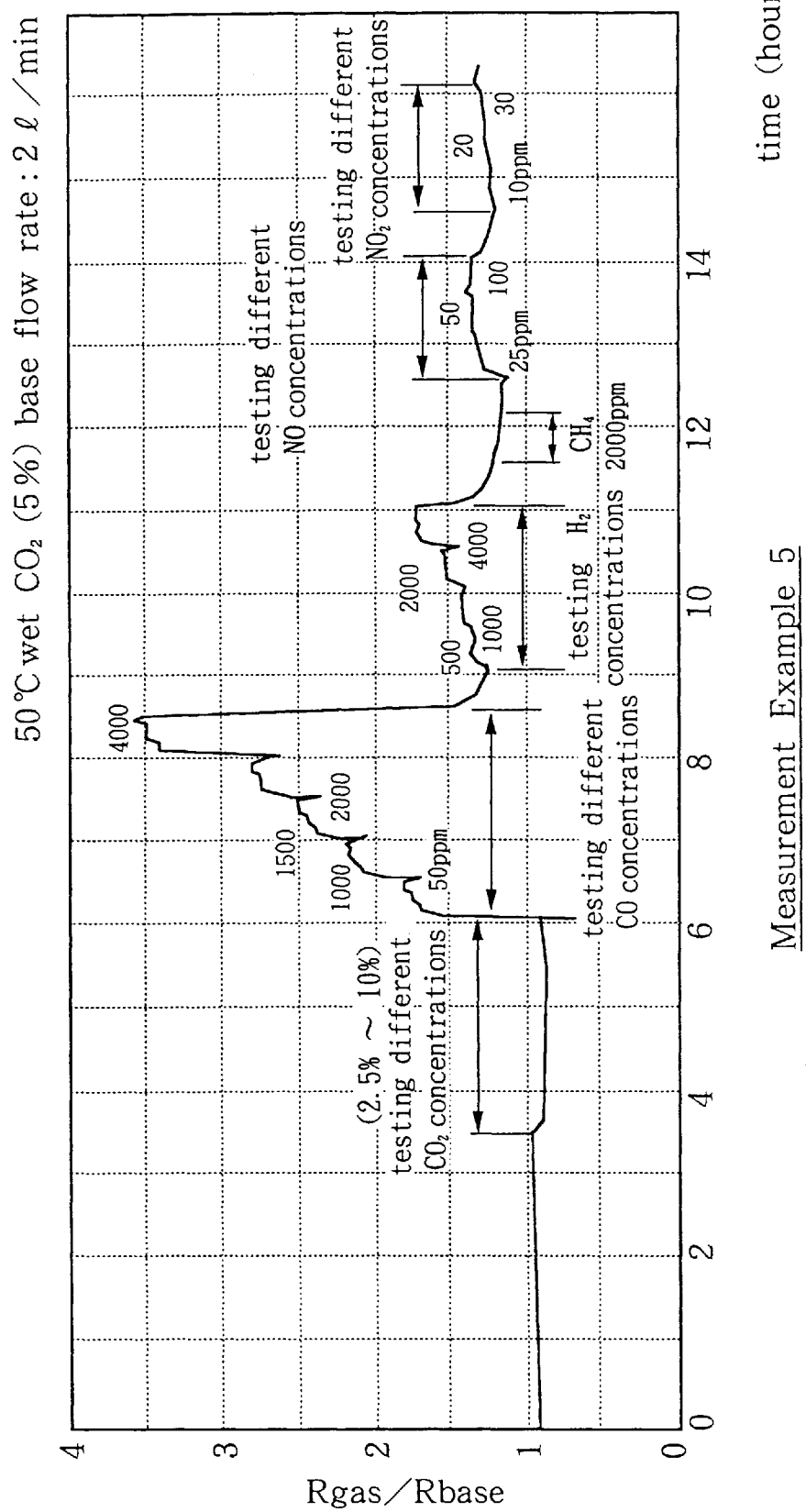
FIG. 22 shows an example of the results of measurements of the sensitivity to various test gases of a gas sensor fabricated by adding $Na_2WO_4.2H_2O$ to CuO.

FIG. 22 shows the results of measurements of sensitivity to various test gases. For these measurements, the apparatus illustrated in FIG. 10 was used, and instead of being heated externally, gas sensor 40 being measured was heated by means of a heater provided on its rear surface. A voltage of 2.5 V was then applied between the electrodes and measurements made of the ratio of $R_{gas}$ to $R_{base}$ for a sequence of test gases, where $R_{gas}$ is the sensor resistance in the presence of a given test gas, and $R_{base}$ is the sensor resistance in the base condition. The base condition was an atmosphere comprising 5% $CO_2$ and the added water vapor equivalent of the partial pressure of saturated water vapor at 50° C. and atmospheric pressure. $CO_2$, CO, $H_2$, $CH_4$, NO and $NO_2$ were used as the test gases. The measurements were made under two $CO_2$ conditions: a first in which only $CO_2$ was tested and the $CO_2$ concentration was varied within the range 2.5–10%, and a second in which another test gas was added to 5% $CO_2$. The test gases were used in the following concentrations: 500, 1000, 1500, 2000 and 4000 ppm for CO; 500, 1000, 2000 and 4000 ppm for $H_2$; 2000 ppm for $CH_4$; 25, 50 and 100 ppm for NO; and 10, 20 and 30 ppm for $NO_2$, and these gas concentrations were changed stepwise. It will be seen from the measurement results that there was hardly any sensitivity to $CO_2$, and that CO selectivity was very high.

MEASUREMENT EXAMPLE 6

Figure 23:
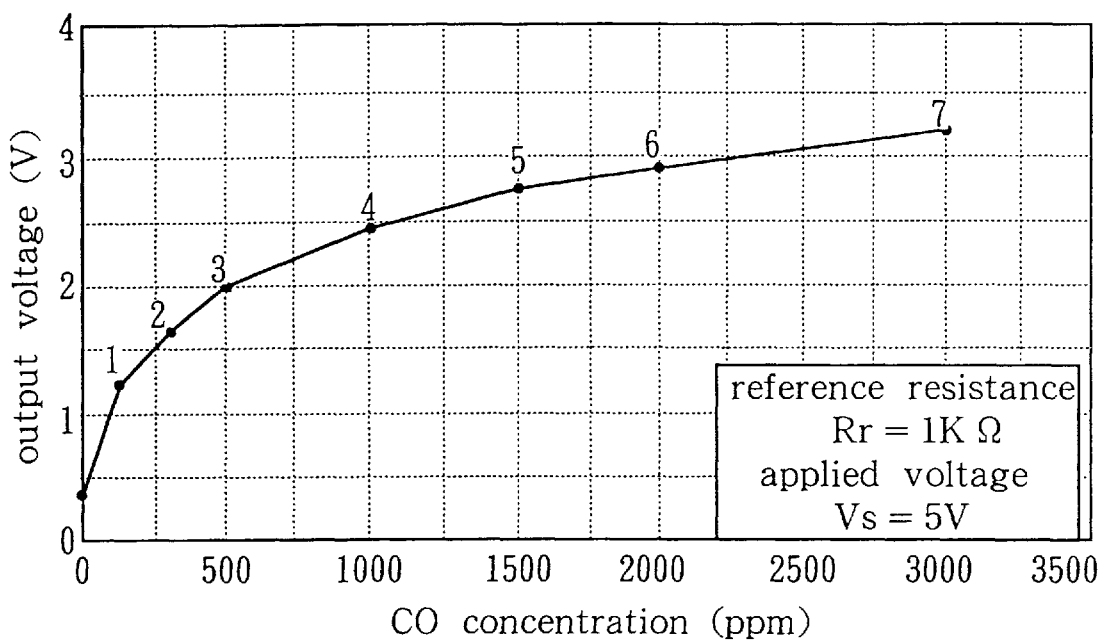
FIG. 23 shows an example of the results of measurements of changes in the terminal voltage of a gas sensor in a gas composition simulating the exhaust gases of a water heater during incomplete combustion.
Figure 24:
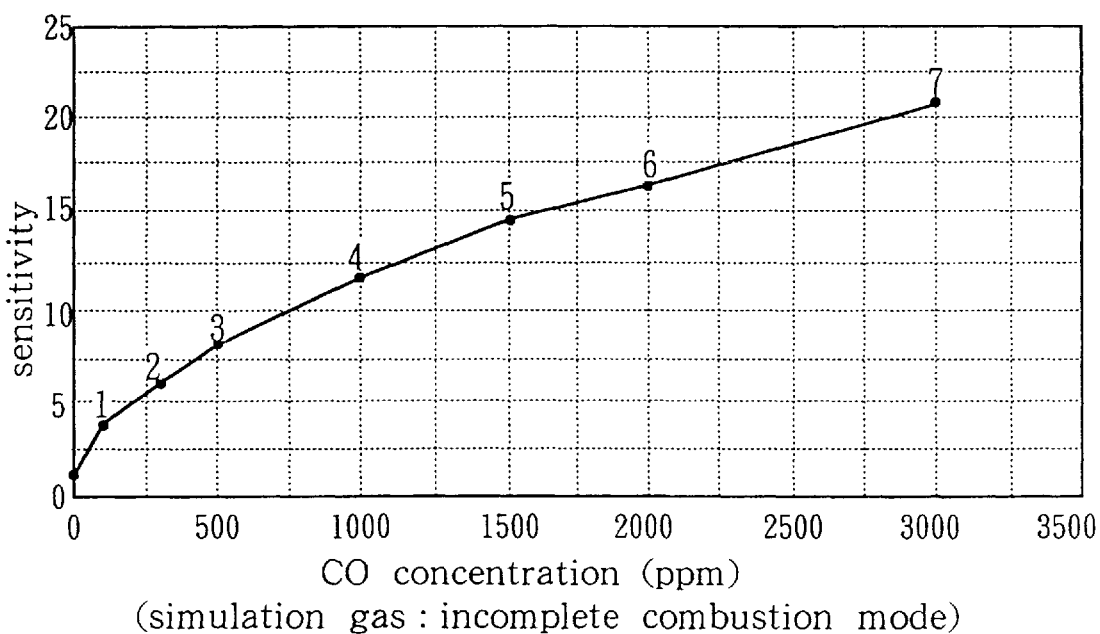
FIG. 24 expresses the measurement results of FIG. 23 as changes in sensitivity.

In order to measure sensor sensitivity during incomplete combustion in a water heater, gas sensors of the type used in Measurement Example 5 were used for measurements of sensitivity characteristics in a gas composition designed to simulate the exhaust gases resulting from incomplete combustion. The composition of the simulation gas is given in Table 1, and the results of the measurements are shown in FIG. 23 and FIG. 24. FIG. 23 gives the results obtained when a voltage of 5 V was applied across a series-connected 1 kΩ reference resistance Rr and the gas sensor described above, and measurements made of the changes in sensor terminal voltage as a function of CO concentration. FIG. 24 shows these measurement results as changes in sensitivity (i.e., the ratio of the resistance change) due to changes in CO concentration. The measurements of voltage change revealed that voltage changed considerably up to the onset of incomplete combustion (a state corresponding to a CO concentration of approximately 2000–4000 ppm), thereby indicating that measurement of voltage change is effective for detecting incomplete combustion. In practice, the output of the gas sensor can also be utilized after correction by a microprocessor or the like.

MEASUREMENT EXAMPLE 7

Figure 25:
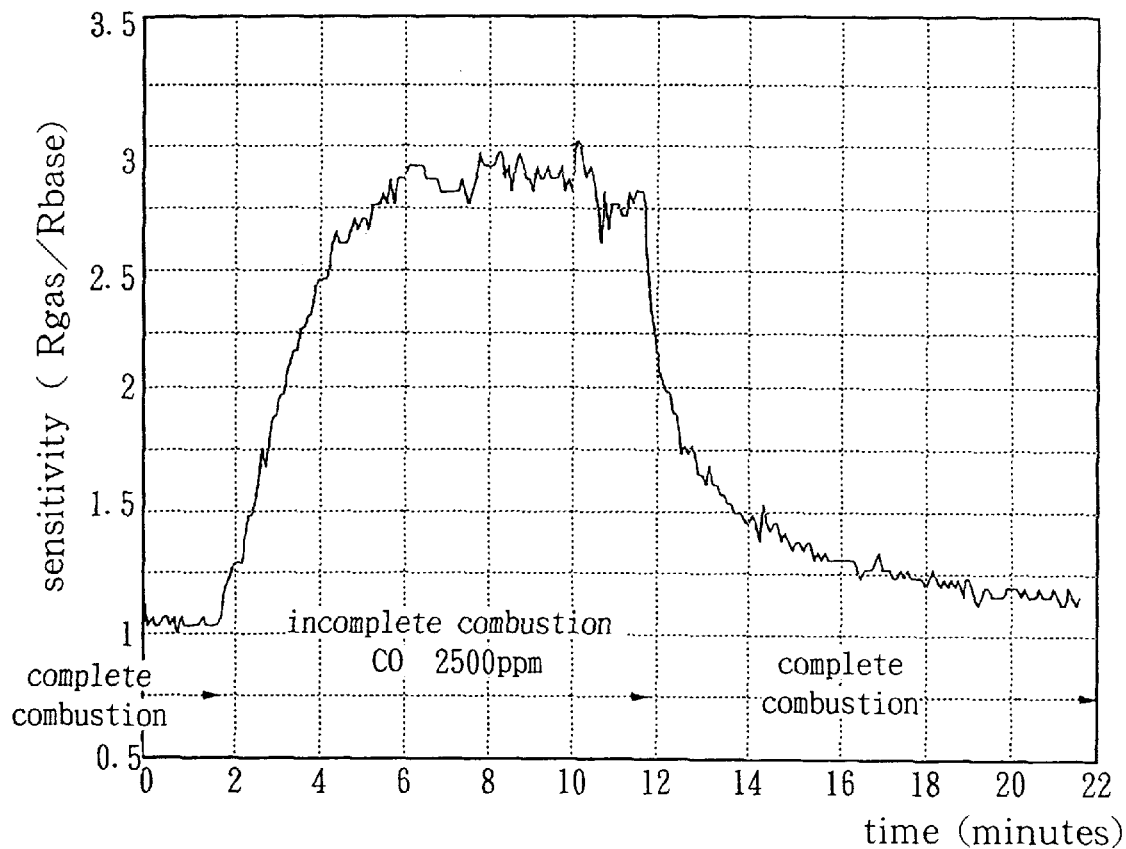
FIG. 25 shows an example of sensor output characteristics during incomplete combustion in a gas-fired water heater of forced draft type.

Sensor output characteristics during incomplete combustion in a forced draft type gas-fired water heater such as shown in FIG. 6 were measured using gas sensors of the type employed in Measurement Examples 5 and 6. The results of these measurements are shown in FIG. 25. The vertical axis shows the ratio of $R_{gas}$, sensor resistance during combustion, to $R_{base}$, sensor resistance when air is blown through the heater. Incomplete combustion is equivalent to a CO concentration of the order of 2500 ppm. FIG. 25 shows that incomplete combustion can be detected by this gas sensor. Moreover, taking into consideration the measurement results of Measurement Examples 5 and 6 (FIG. 23 and FIG. 24), it will be seen that this gas sensor detects mainly CO gas.

MEASUREMENT EXAMPLE 8

A 2 mm×3 mm×1 mm sintered mass was obtained by adding 8 wt % $Na_2WO_4 \cdot 2H_2O$ to CuO and firing at a maximum temperature of 600° C. Four gas sensors each having the structure shown in FIG. 1 to FIG. 3 were fabricated using this mass just as it was and attaching electrodes to the 2 mm×3 mm faces. These four gas sensors were then used for measurements of sensor resistance as a function of the concentration of CO, $H_2$, $O_2$, water vapour and NO. The results are shown in FIG. 26 to FIG. 30. At any given concentration, the measured values obtained by the four gas sensors are nearly the same, and FIG. 26 to FIG. 30 show the range of these measured values.

Figure 26:
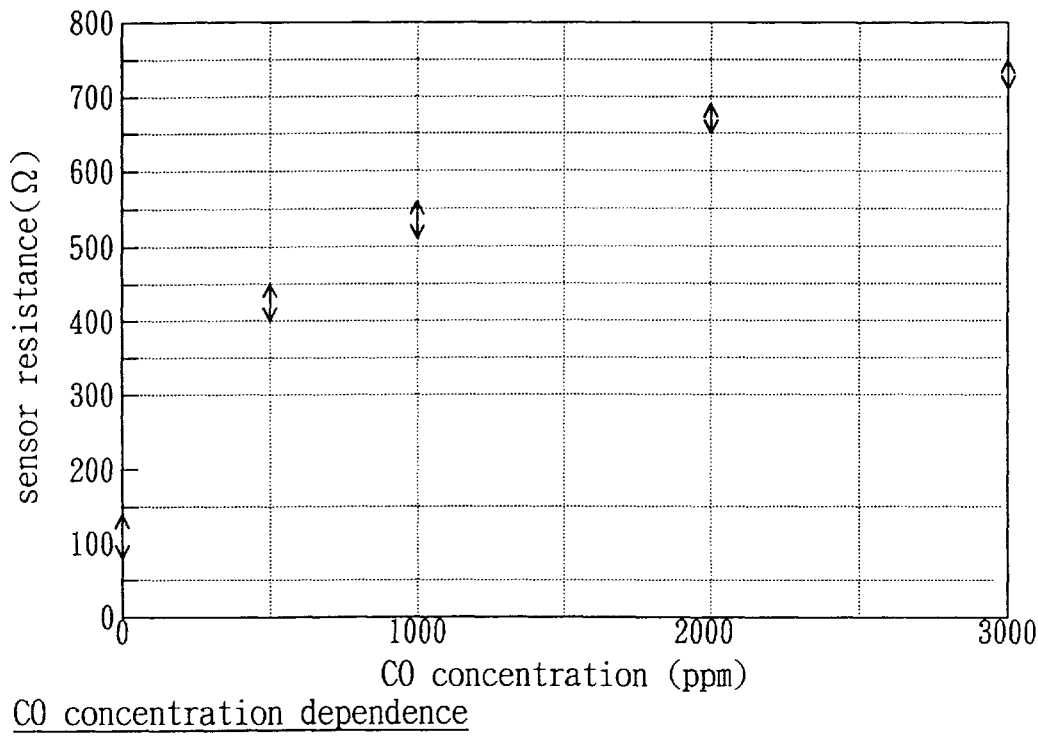
FIG. 26 shows sensor resistance as a function of CO concentration.

FIG. 26 shows sensor resistance as a function of CO concentration. For these measurements, the base gas was an atmosphere comprising $N_2$ to which 7.5% $CO_2$, 7.5% $O_2$, and the water vapour equivalent of the partial pressure of saturated water vapour at 50 ° C. and atmospheric pressure (12% water vapour) had been added. For a CO concentration at 500 ppm, the test gas used comprised 500 ppm of CO and 250 ppm of $H_2$. For a CO concentration of 1000 ppm, the test gas comprised 1000 ppm CO and 500 ppm $H_2$. For a CO concentration of 2000 ppm the test gas comprised 2000 ppm CO and 1000 ppm $H_2$, and for a CO concentration of 3000 ppm it comprised 3000 ppm CO and 1500 ppm $H_2$.

Figure 27:
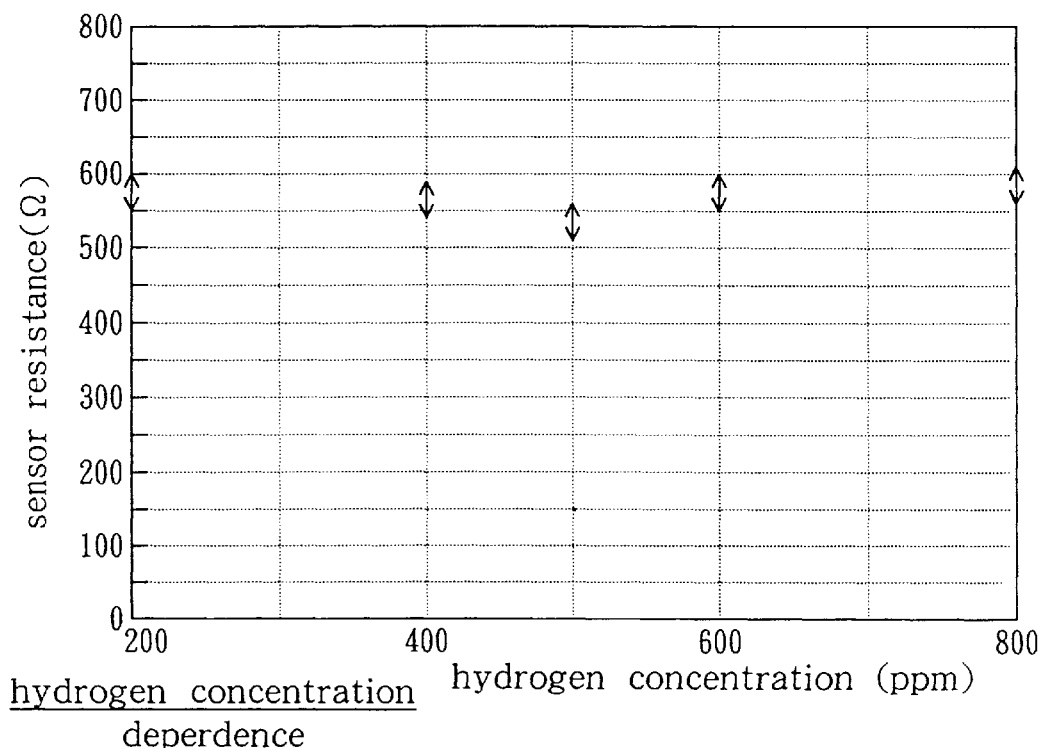
FIG. 27 shows sensor resistance as a function of $H_2$ concentration.

FIG. 27 shows sensor resistance as a function of $H_2$ concentration. For these measurements, 1000 ppm of CO was added to a base gas comprising $N_2$ to which 7.5% $CO_2$, 7.5% $O_2$ and 12% water vapour had been added, and the $H_2$ concentration was varied from 200 to 800 ppm.

Figure 28:
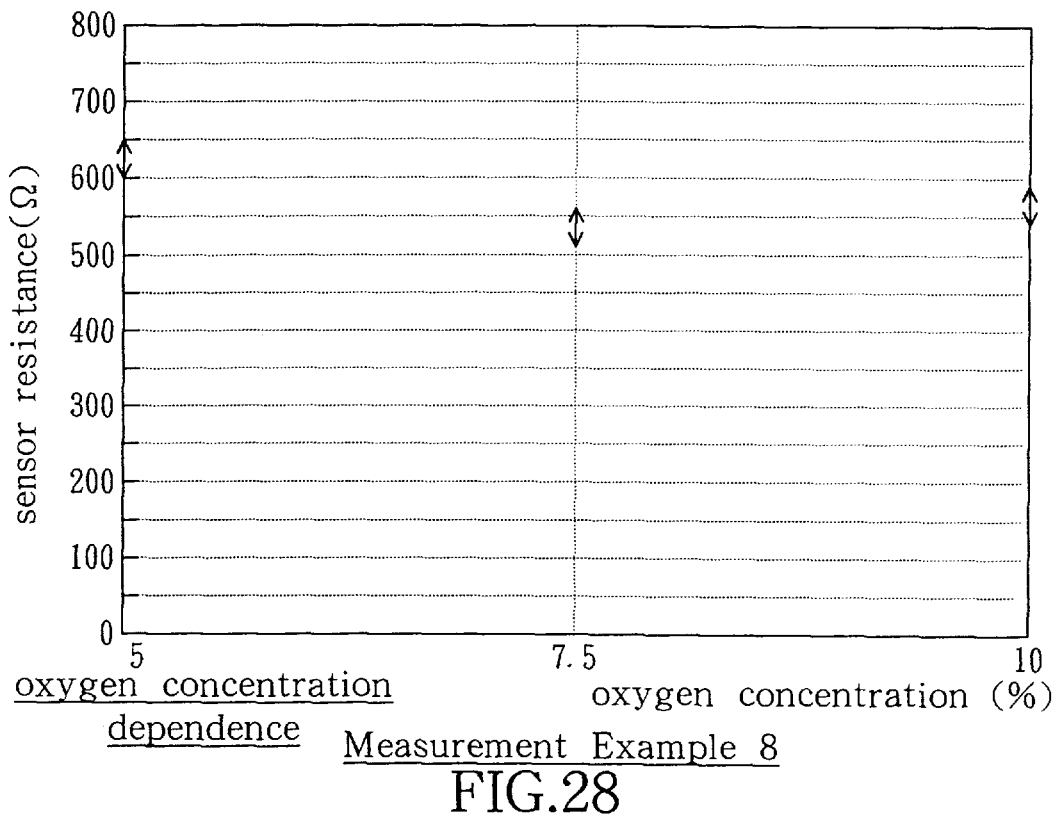
FIG. 28 shows sensor resistance as a function of water vapor concentration.

FIG. 28 shows sensor resistance as a function of $O_2$ concentration. For these measurements, 1000 ppm of CO and 500 ppm of $H_2$ were added to a base gas comprising $N_2$ to which 7.5% $CO_2$ and 12% water vapour had been added, and the $O_2$ concentration was varied from 5 to 10%.

Figure 29:
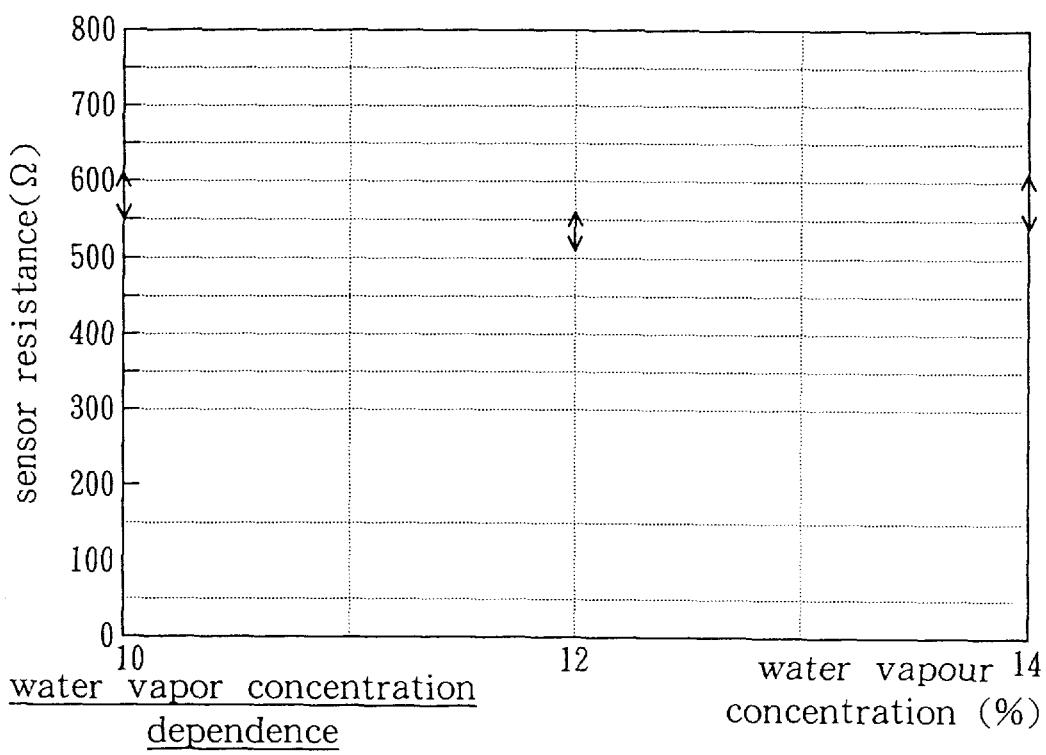
FIG. 29 shows sensor resistance as a function of $H_2$ concentration.

FIG. 29 shows sensor resistance as a function of water vapour concentration. For these measurements, 1000 ppm of

TABLE 1

| simulation gas | No. | NO ppm | $NO_2$ ppm | $SO_2$ ppm | $CH_4$ ppm | $CO_2$ % | $O_2$ % | CO ppm | $H_2$ ppm | water vapor mm Hg |
|---|---|---|---|---|---|---|---|---|---|---|
| normal | 1 | 30 | 10 | 5 | 20 | 7 | 9.5 | 125 | 0 | 90 |
|  | 2 | 40 | 15 | 5 | 10 | 7 | 8 | 300 | 65 | 90 |
|  | 3 | 50 | 15 | 5 | 5 | 8 | 7 | 500 | 200 | 90 |
|  | 4 | 60 | 15 | 5 | 5 | 8 | 6.5 | 1000 | 500 | 90 |
| incomplete combustion | 5 | 60 | 15 | 5 | 5 | 8 | 6 | 1500 | 800 | 90 |
|  | 6 | 65 | 15 | 5 | 5 | 8.5 | 6 | 2000 | 1100 | 90 |
|  | 7 | 70 | 15 | 5 | 5 | 8.5 | 5 | 3000 | 2000 | 90 |

CO and 500 ppm of $H_2$ were added to a base gas comprising $N_2$ to which 7.5% $CO_2$ and 7.5% $O_2$ had been added, and water vapour was varied from 10 to 14%.

Figure 30:
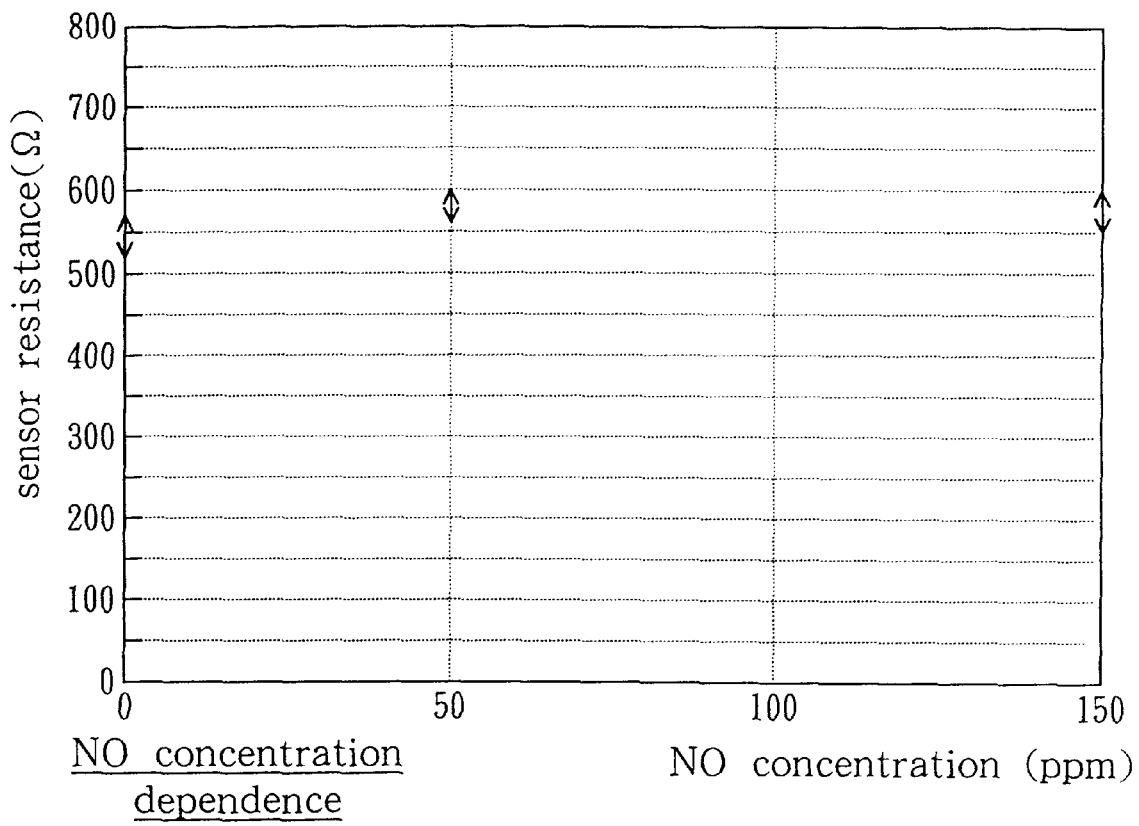
FIG. 30 shows sensor resistance as a function of NO concentration.

FIG. 30 shows sensor resistance as a function of NO concentration. For these measurements, 1000 ppm of CO and 500 ppm of $H_2$ were added to a base gas comprising $N_2$ to which 7.5% $CO_2$, 7,5% $O_2$ and 12% water vapour had been added, and the NO concentration was varied from 0 to 150 ppm.

These measurement results show that the change in sensor resistance as a function of CO concentration is larger than its changes as functions of the concentration of $H_2$, $O_2$, water vapour and NO, thereby indicating suitability for detection of CO gas.

MEASUREMENT EXAMPLE 9

Figure 31:
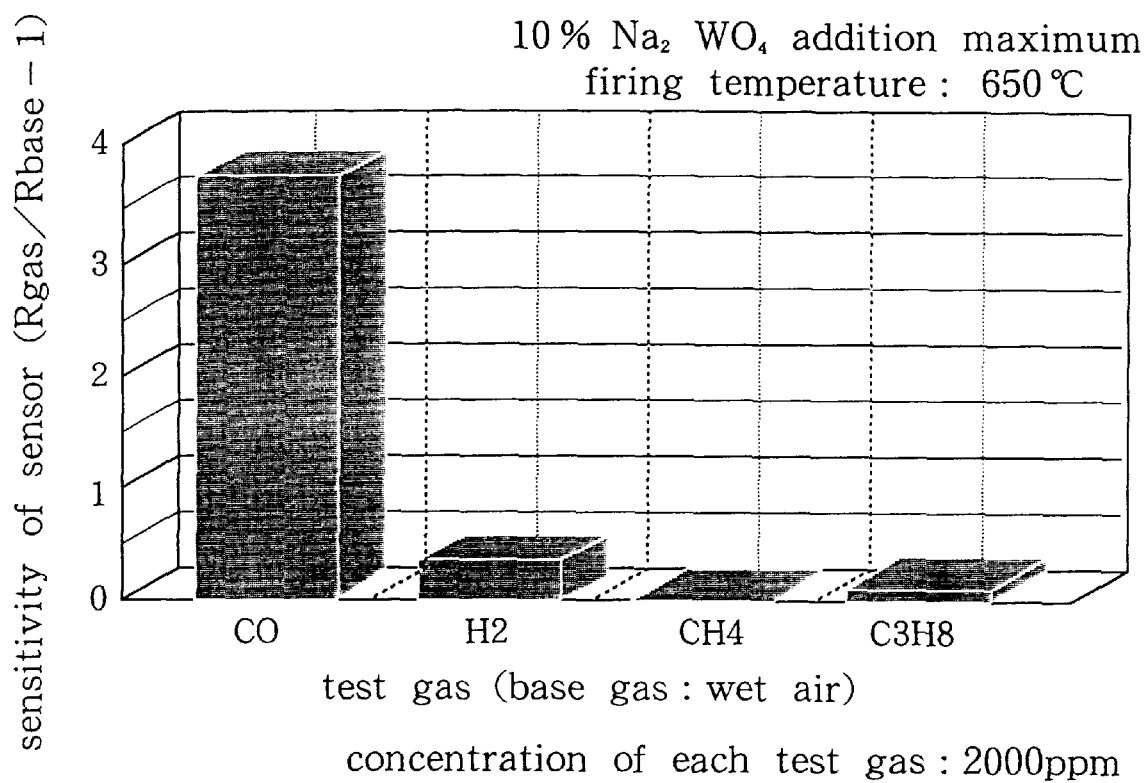
FIG. 31 shows the results of measurements of sensitivity to CO, $H_2$, $CH_4$ and $C_3H_8$.

10 wt % of $Na_2WO_4.2H_2O$ was added to CuO and the resulting mixture fired at a maximum temperature of 650° C. A gas sensor with the same structure as in Measurement Example 5 was fabricated by cutting the sintered mass obtained and attaching electrodes. The sensitivity of this gas sensor to CO, $H_2$, $CH_4$ and $C_3H_8$ was then measured. The results are shown in FIG. 31. The base gas used in these measurements was dry air to which water vapour equivalent to saturated water vapour at 25° C. and atmospheric pressure had been added, and the measurements were made with the concentration of each gas set at 2000 ppm. The measurement results given in FIG. 31 show that this gas sensor has a high degree of selectivity for CO gas.

MEASUREMENT EXAMPLE 10

A thick film gas sensor with the structure shown in FIG. 4 and FIG. 5 was fabricated by forming a paste comprising 5 wt % of $Na_2WO_4$ (anhydride) added to CuO, screen printing this onto interdigitated electrodes, and firing at a maximum temperature of 650° C. An alumina substrate was used as ceramic substrate 24, and a heater for heating the sensor was provided on the rear surface.

Figure 32:
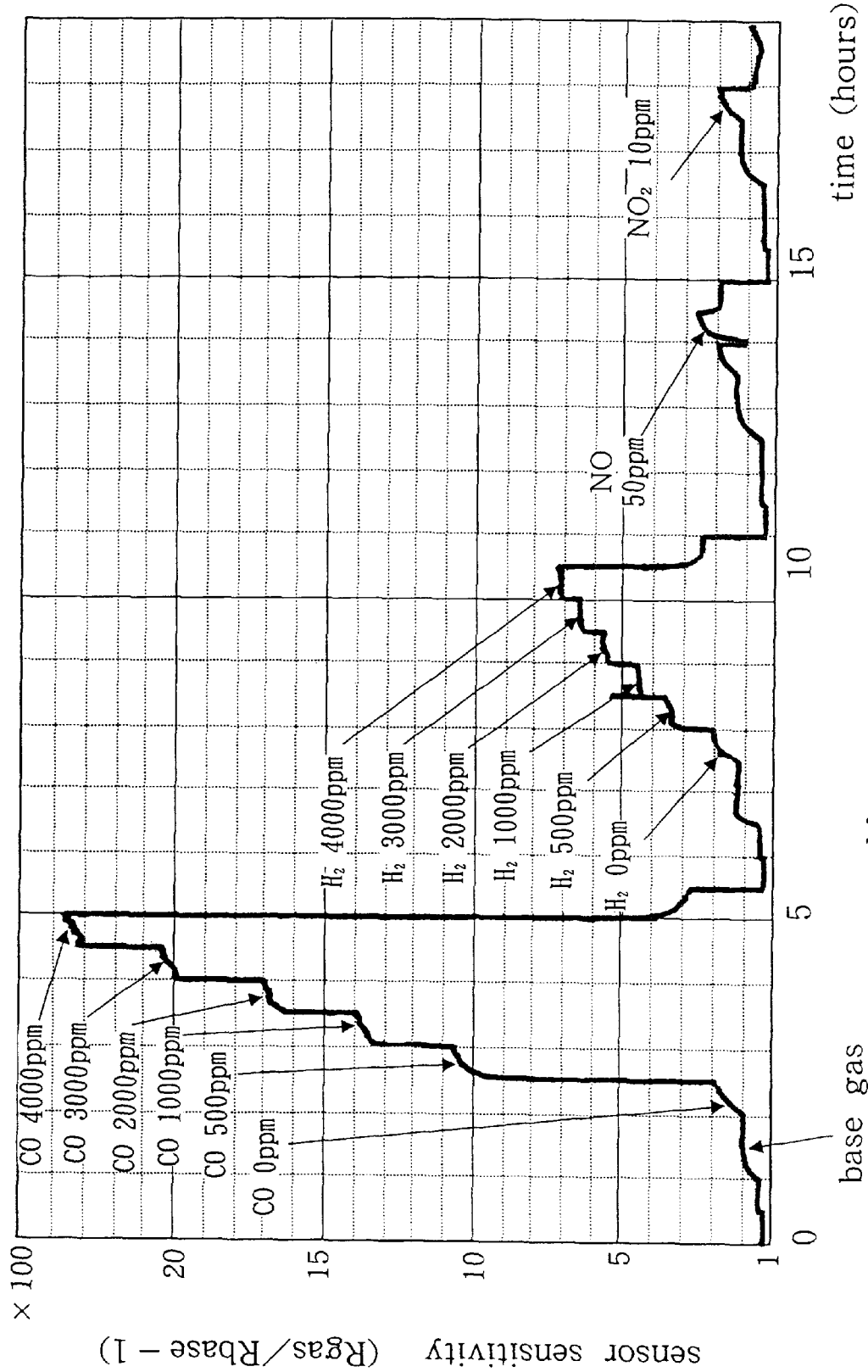
FIG. 32 shows the results of measurements of sensitivity to various test gases.

FIG. 32 shows the results of measurements of sensitivity to various test gases. These measurements were performed in the same manner as in Measurement Example 5, using 7.5% $CO_2$, 7.5% $O_2$ and 12% water vapour added to $N_2$ as the base gas, and 500, 1000, 2000, 3000 and 4000 ppm of CO; 500, 1000, 2000, 3000 and 4000 ppm of $H_2$; 50 ppm of NO, and 10 ppm of $NO_2$ as the test gases. These measurement results show that the CO selectivity is very high.

MEASUREMENT EXAMPLE 11

Figure 33:
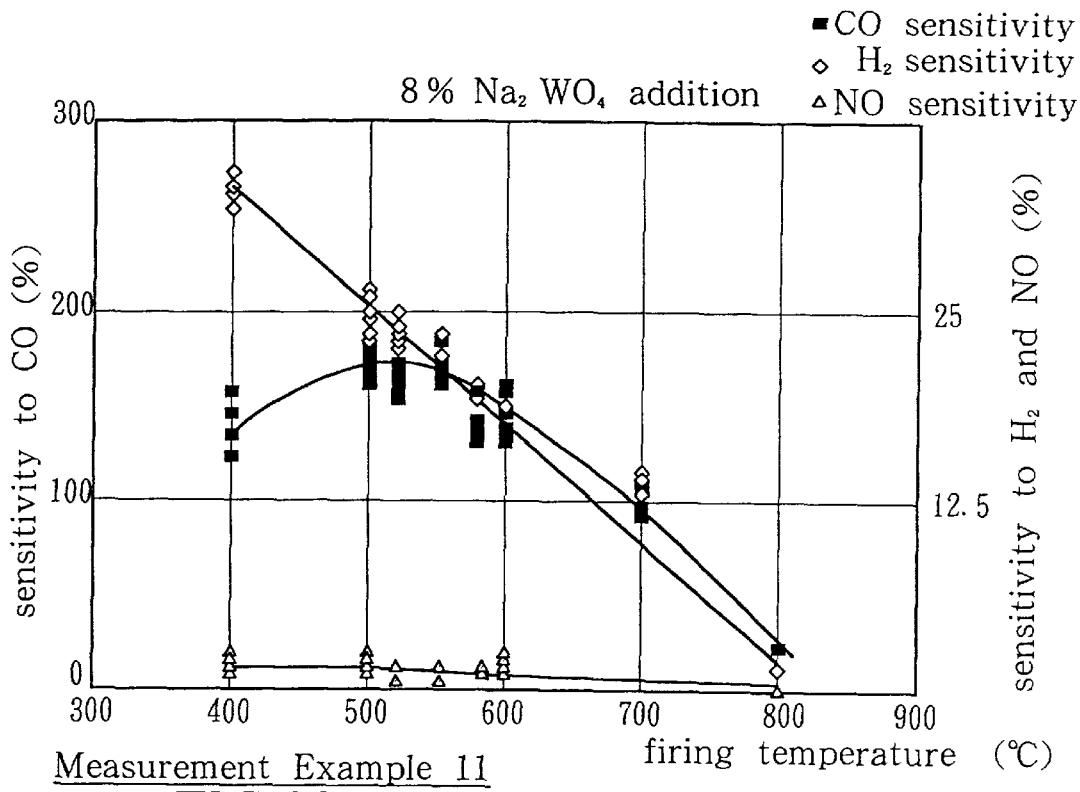
FIG. 33 shows the results of measurements of gas sensitivity as a function of maximum temperature during firing.

Gas sensors with the same structure as in Measurement Example 1 (see FIG. 12 to FIG. 14) were fabricated by adding 8 wt % of $Na_2WO_4.2H_2O$ to CuO and firing at a variety of firing temperatures. Measurements were then made of gas sensitivity as a function of maximum firing temperature. The results are shown in FIG. 33. Air with a $CO_2$ concentration of 5% was used as the base gas, and 4000 ppm of CO, 4000 ppm of $H_2$ and 50 ppm of NO were used as the test gases. The vertical axis on the left-hand side of FIG. 33 shows CO sensitivity, while the vertical axis on the right-hand side shows $H_2$ sensitivity and NO sensitivity. A satisfactorily high CO sensitivity is obtained if the maximum firing temperature is 400° C. or over, but there is a conspicuous decrease in CO sensitivity if the maximum firing temperature exceeds 500° C. (at which temperature the strength of the sintered mass is high). Provided that the maximum firing temperature is no more than 800° C., the CO sensitivity is higher than the $H_2$ sensitivity.

MEASUREMENT EXAMPLE 12

Figure 34:
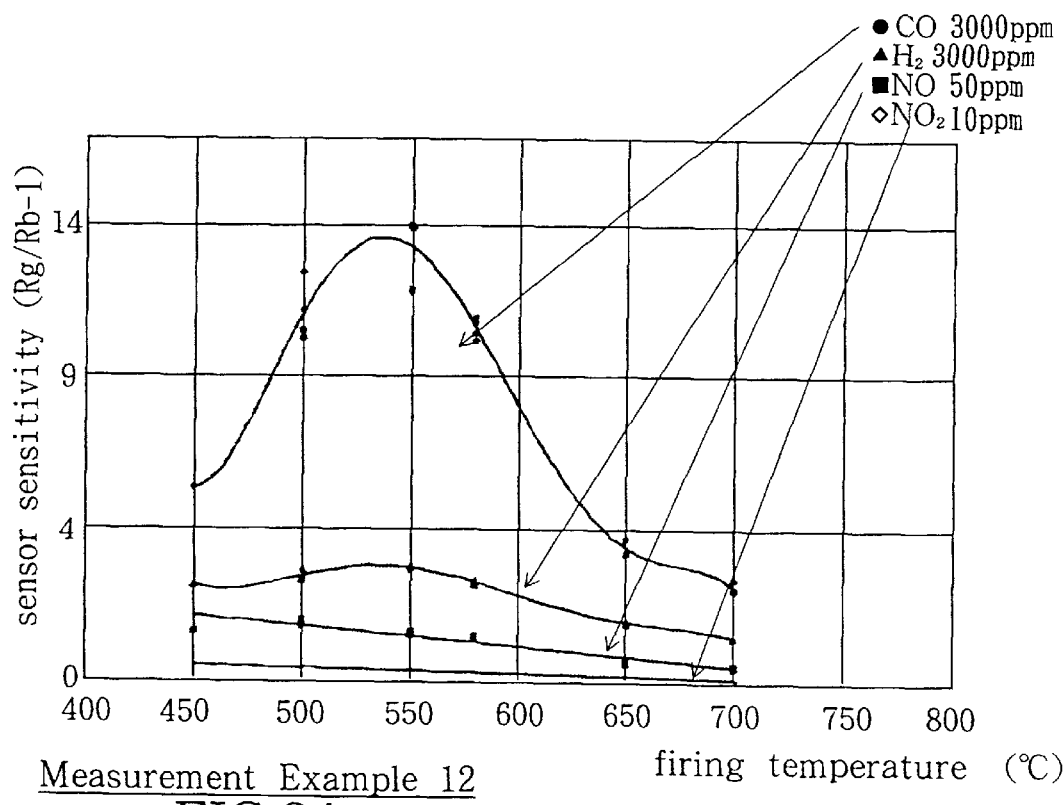
FIG. 34 gives an example of the results of measurements of gas sensitivity as a function of firing temperature.

Thick film gas sensors of the same construction as in Measurement Example 10 were fabricated using a paste comprising 5 wt % $Na_2WO_4$ (anhydride) added to CuO, and employing a variety of firing temperatures. Measurements were then made of gas sensitivity as a function of maximum firing temperature. The results are shown in FIG. 34. $N_2$ to which 7.5% $CO_2$, 7.5% $O_2$ and 12% water vapour had been added was used as the base gas, and 3000 ppm of CO, 3000 ppm of $H_2$, 50 ppm of NO and 10 ppm of $NO_2$ were used as the test gases. It will be seen from these measurement results that satisfactorily high CO sensitivity is obtained if the firing temperature is 450° C. or over, but that there is a pronounced decrease in CO sensitivity if the firing temperature exceeds 550° C. Provided that the firing temperature is no more than 700° C., the CO sensitivity is higher than the $H_2$ sensitivity.

MEASUREMENT EXAMPLE 13

Figure 35:
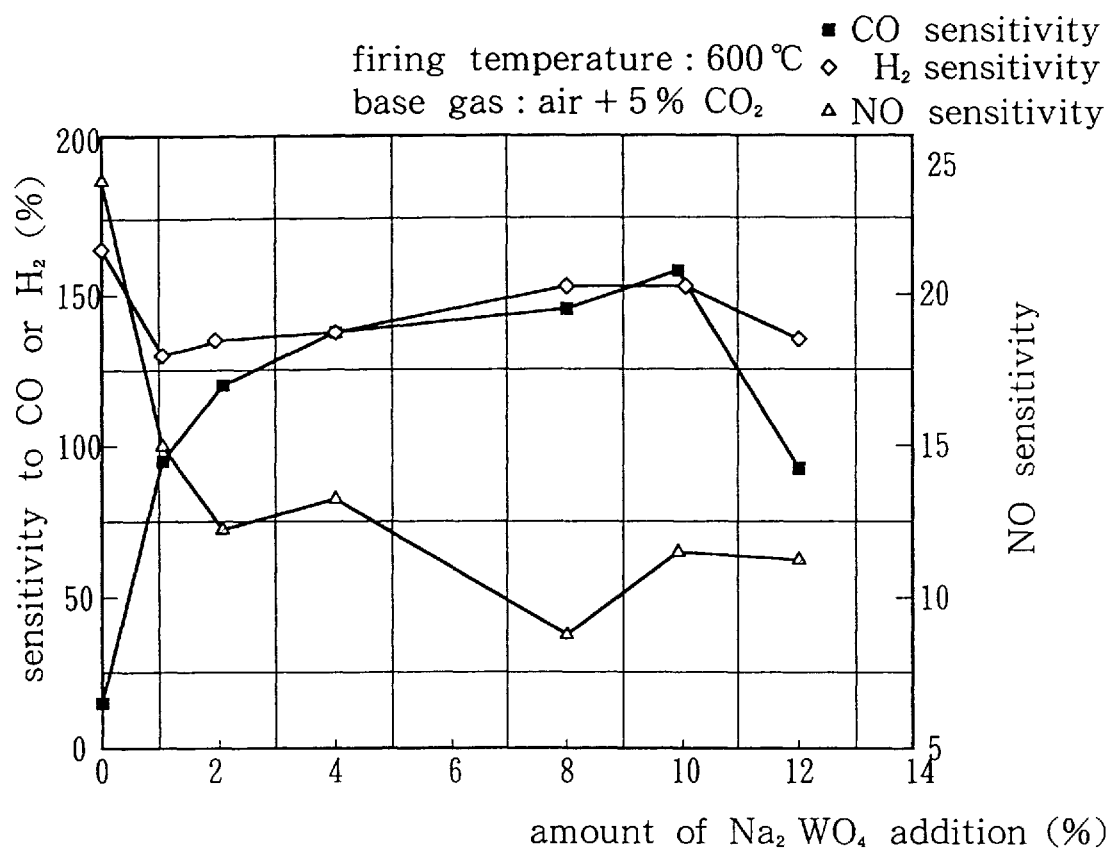
FIG. 35 gives an example of the results of measurements of gas sensor sensitivity as a function of the amount of $Na_2WO_4$ addition.

Gas sensors were fabricated with different amounts of $Na_2WO_4.2H_2O$ addition, and their sensitivity measured. The maximum firing temperature was set at 600° C. The structure of the gas sensors was the same as in Measurement Example 12 (see FIG. 12 to FIG. 14). The results of these measurements are shown in FIG. 35. Air with a $CO_2$ concentration of 5% was used as the base gas, and 4000 ppm of CO, 4000 ppm of $H_2$, and 50 ppm of NO were used as the test gases. The vertical axis on the left-hand side of FIG. 35 shows the CO sensitivity and $H_2$ sensitivity, while the vertical axis on the right-hand side shows NO sensitivity. It will be seen from FIG. 35 that CO sensitivity increases remarkably when the amount of addition of the $Na_2WO_4.2H_2O$ is 2 wt % or more.

MEASUREMENT EXAMPLE 14

Figure 36:
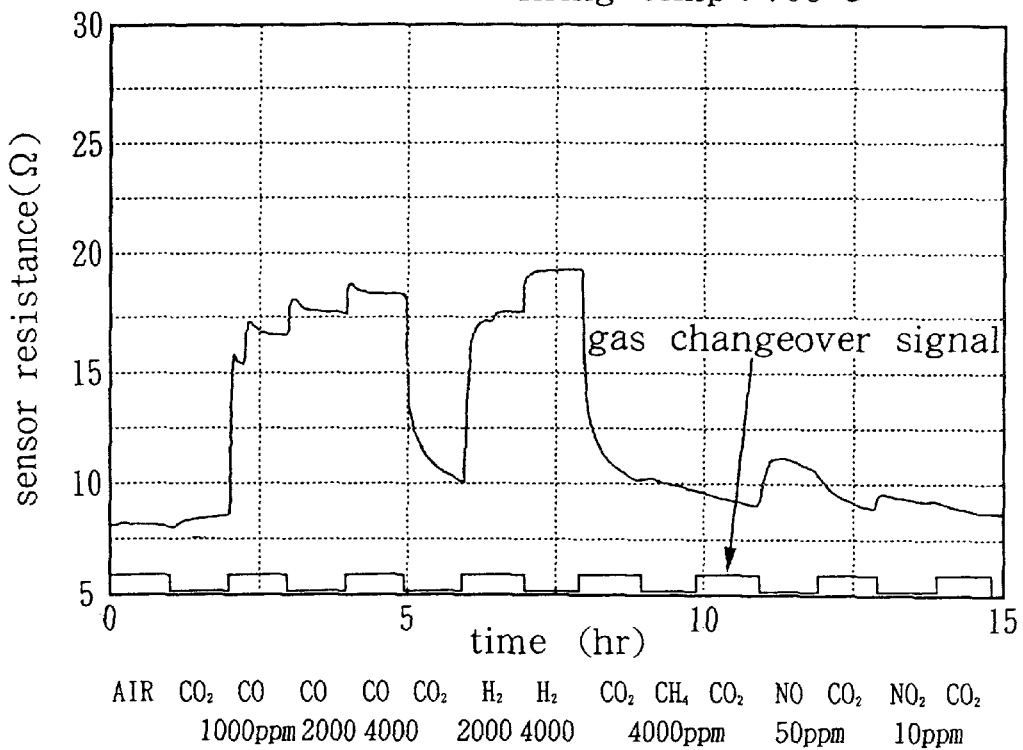
FIG. 36 gives an example of the results of measurements of resistance as a function of test gas, for a gas sensor in which $Na_2MoO_4.2H_2O$ has been added to CuO.

A gas sensor was fabricated by adding 10 wt % of $Na_2MoO_4.2H_2O$ to CuO, firing at a maximum temperature of 700° C., and attaching electrodes to the sintered mass thereby obtained. Measurements were then made of the resistance of this sensor. The structure of the sensor was the same as in Measurement Example 12 (see FIG. 12 to FIG. 14). The measurement results are shown in FIG. 36. Air with a $CO_2$ concentration of 5% was used as the base gas, and 1000, 2000 and 4000 ppm of CO, 2000 and 4000 ppm of $H_2$, 4000 ppm of $CH_4$, 50 ppm of NO, and 10 ppm of $NO_2$ were used as the test gases. An initial measurement was also made for air only, and it was found that there was a small change in sensor resistance according to whether $CO_2$ was present or not. Although the $H_2$ sensitivity of this gas sensor is close to the CO sensitivity, it is fully capable of detecting actual incomplete combustion.

MEASUREMENT EXAMPLE 15

Figure 37:
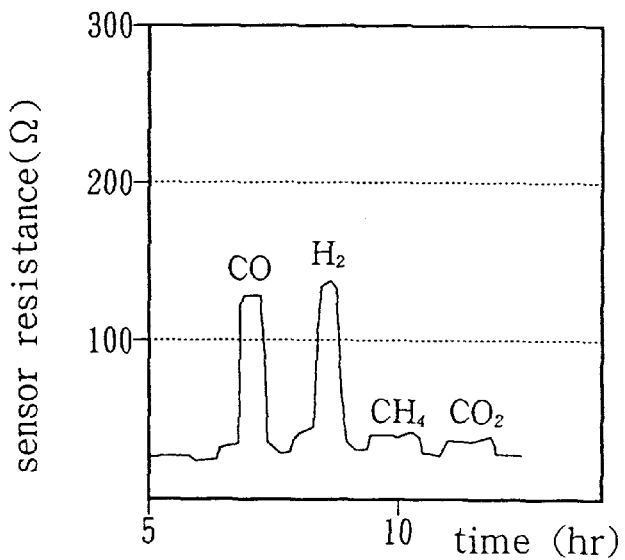
FIG. 37 gives an example of the results of measurements when the structure of the gas sensor used for FIG. 28 was changed.

A gas sensor with the same structure as in Measurement Example 5 (see FIG. 1 to FIG. 3) was fabricated from a sintered mass which had been fired under the same conditions as Measurement Example 14, and measurements were made of its resistance. The results of these measurements are given in FIG. 37. Air was used as the base gas, and 4000 ppm of CO, 4000 ppm of $H_2$, 4000 ppm of $CH_4$ and 5% $CO_2$ were used as the test gases.

MEASUREMENT EXAMPLE 16

Figure 38:
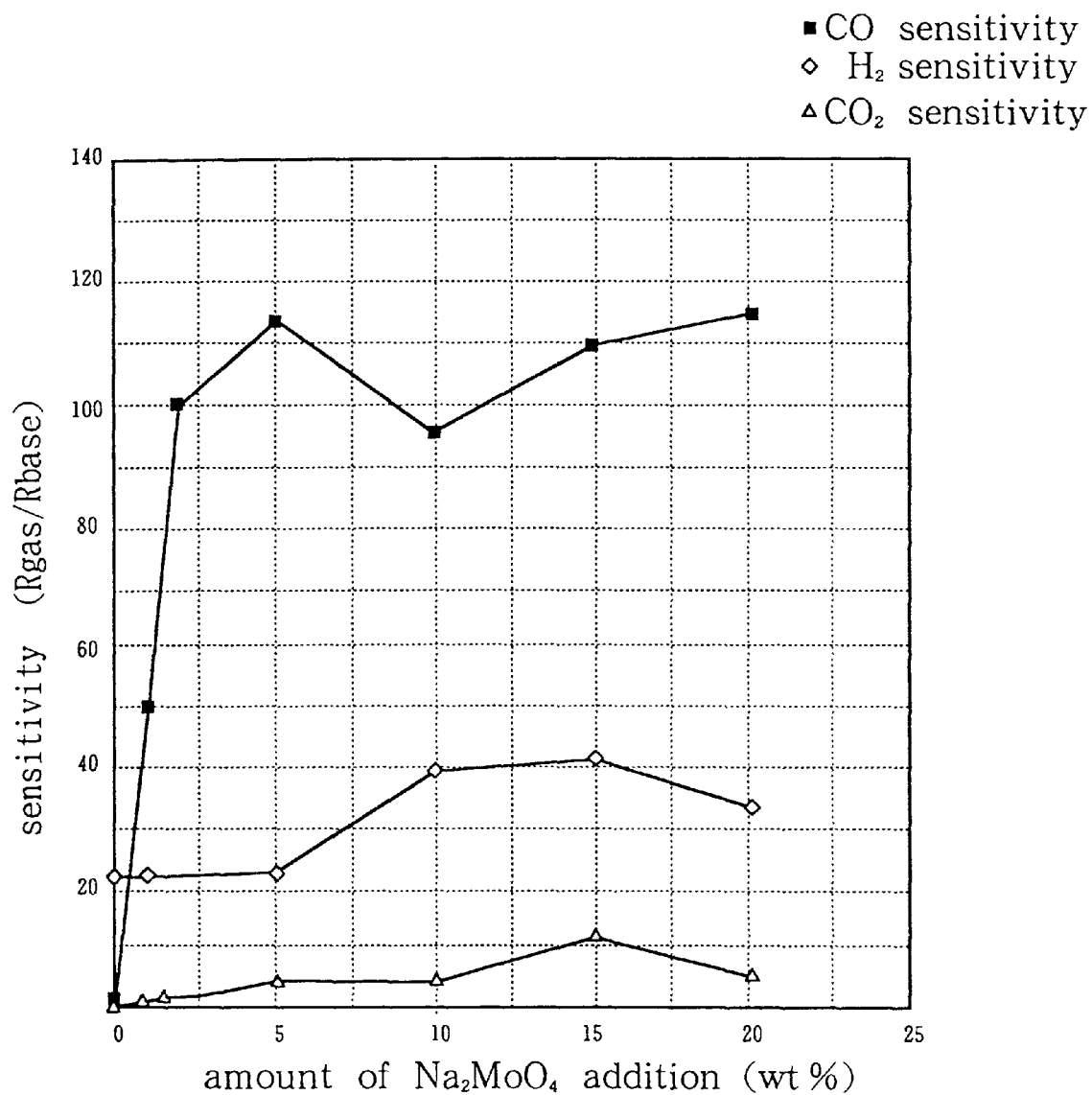
FIG. 38 gives an example of the results of measurements of sensitivity as a function of the amount of $Na_2MoO_4$ added.

Gas sensors were fabricated with different amounts of $Na_2MoO_4.2H_2O$ addition, and measurements made of the resulting changes in sensitivity. The maximum firing temperature was set at 600° C. and the structure of the sensors was the same as in Measurement Example 12 (see FIG. 12 to FIG. 14). The results of these measurements are shown in FIG. 38. Air was used as the base gas, and 4000 ppm of CO, 4000 ppm of $H_2$, and 5% $CO_2$ were used as the test gases. These measurement results show that CO sensitivity increases remarkably when the amount of addition is greater than 1 wt %.

We claim:

1. A gas sensor comprising:
a p-type member formed from a p-type semiconductor, said p-type semiconductor having CuO as a main constituent; and
two electrodes connected to said p-type member, said electrodes being constructed and arranged to extract changes in electrical characteristics resulting from the presence of a gas to be detected,
wherein said p-type semiconductor comprises, as an additive, $Na_2CO_3$ in excess of 1 wt % relative to CuO.

2. A gas sensor according to claim 1, wherein said additive $Na_2CO_3$ is present in a concentration of not more than 40 wt % relative to CuO.

3. A gas sensor according to claim 1, wherein said additive $Na_2CO_3$ is present in a concentration of not more than 20 wt % relative to CuO.

4. A method for manufacturing a gas sensor comprising a member with electrical characteristics which change in accordance with the presence of a gas to be detected, said method comprising:
adding to powdered CuO a $Na_2CO_3$ precursor; and
molding and firing the powdered CuO and the $Na_2CO_3$ precursor to convert the precursor to $Na_2CO_3$,
wherein the $Na_2CO_3$ precursor is added in an amount to attain a content of $Na_2CO_3$ that exceeds 1 wt % relative to CuO.

5. A method according to claim 4, wherein the powdered CuO has primary particles with a specific surface area of at least 2 $m^2/g$.

6. A method according to claim 4, wherein the powdered CuO has primary particles with a specific surface area of at least 20 $m^2/g$.

7. A method according to claim 4, wherein the powdered CuO has primary particles with particle sizes of no more than 1 $\mu m$.

8. A method according to claim 4, wherein the powdered CuO has primary particles with particle sizes of no more than 0.25 $\mu m$.

9. A method according to claim 4, wherein said firing is performed at a maximum temperature of at least 400° C.

10. A method according to claim 9, wherein said firing is performed at a maximum temperature of no more than 860° C.

11. A method according to claim 10, wherein said firing is performed at a maximum temperature of at least 500° C. and no more than 700° C.

12. A gas sensor comprising:
a p-type member formed from a p-type semiconductor, said p-type semiconductor having a sodium compound and, as a main constituent, CuO; and
two electrodes connected to said p-type member, said electrodes being constructed and arranged to extract changes in electrical characteristics resulting from the presence of a gas to be detected,
wherein said sodium compound comprises a sodium salt of at least one acid selected from the group comprising tungstic acid and molybdic acid.

13. A gas sensor according to claim 12, said gas sensor containing as said sodium compound a sodium salt of tungstic acid at from 0.5 to 23 wt % as tungsten relative to CuO.

14. A gas sensor according to claim 12, said gas sensor containing as said sodium compound a sodium salt of molybdic acid at from 0.4 to 16 wt % as molybdenum relative to CuO.

15. A method for manufacturing a gas sensor comprising a member with electrical characteristics which change in accordance with the presence of a gas to be detected, said method comprising:
adding a sodium compound to CuO and then molding and firing the sodium compound and CuO to convert the sodium compound to a sodium salt of at least one acid selected from the group consisting of tungstic acid and molybdic acid.

16. A method according to claim 15, wherein said adding step comprises adding the sodium compound in an amount to obtain the sodium salt of tungstic acid at from 0.5 to 23 wt % as tungsten relative to CuO.

17. A method according to claim 16, wherein said adding step comprises adding $Na_2WO_4.2H_2O$ at 1 to 40 wt % relative to CuO.

18. A method according to claim 15, wherein said adding step comprises adding the sodium compound in an amount to obtain the sodium salt of molybdic acid at from 0.4 to 16 wt % as molybdenum relative to CuO.

19. A method according to claim 18, wherein said adding step comprises adding $Na_2MoO_4.2H_2O$ at 1 to 40 wt % relative to CuO.

20. A method according to claim 15, wherein said firing is performed at a maximum temperature of at least 400° C.

21. A method according to claim 20, wherein said firing is performed at a maximum temperature of no more than 860° C.

22. A method according to claim 20, wherein said firing is performed at a maximum temperature of at least 500° C. and no more than 850° C.

* * * * *